United States Patent

Lorenz et al.

[11] Patent Number: 5,922,648
[45] Date of Patent: Jul. 13, 1999

[54] 2-AMINO-1,3,5-TRIAZINES, AND THEIR USE AS HERBICIDES AND PLANT GROWTH REGULATORS

[75] Inventors: Klaus Lorenz, Weiterstadt; Klemens Minn, Hattersheim; Lothar Willms, Hofheim; Klaus Bauer, Hanau; Hermann Bieringer, Eppstein; Christopher Rosinger, Hofheim, all of Germany

[73] Assignee: Hoechst Schering AgrEvo GmbH, Berlin, Germany

[21] Appl. No.: 08/668,430

[22] Filed: Jun. 17, 1996

[30] Foreign Application Priority Data

Jun. 19, 1995 [DE] Germany ............ 195 22 137

[51] Int. Cl.$^6$ ............ C07D 251/18; A01N 43/68
[52] U.S. Cl. ............ 504/232; 504/219; 504/230; 504/233; 504/234; 540/481; 540/598; 544/113; 544/206; 544/207
[58] Field of Search ............ 504/233, 232, 504/234, 230; 544/206, 207, 113; 540/481, 598

[56] References Cited

U.S. PATENT DOCUMENTS

| 4,932,998 | 6/1990 | Takematsu et al. ............ 544/207 |
| 5,290,754 | 3/1994 | Nishii et al. ............ 504/232 |
| 5,403,815 | 4/1995 | Nishii et al. ............ 504/230 |

FOREIGN PATENT DOCUMENTS

| 0 509 544 | 10/1992 | European Pat. Off. . |
| 0 492 615 | 3/1995 | European Pat. Off. . |
| 0 645 365 | 3/1995 | European Pat. Off. . |
| 88/02368 | 4/1988 | WIPO . |
| WO 90/09378 | 8/1990 | WIPO . |
| 94/24086 | 10/1994 | WIPO . |

*Primary Examiner*—John M. Ford
*Attorney, Agent, or Firm*—Frommer Lawrence & Haug LLP

[57] ABSTRACT

Compounds of the formula (I) and salts thereof

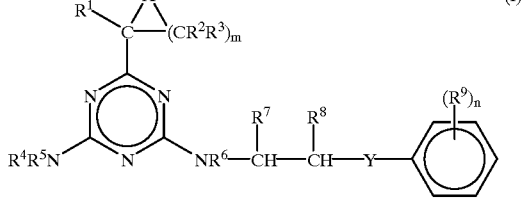

in which $R^1$ to $R^9$, X, Y n and m are as defined in the claim 1 are suitable as herbicides and plant growth regulators. They can be prepared by a process as defined in claim 6, by way of in some cases novel intermediates of the formula (IV)

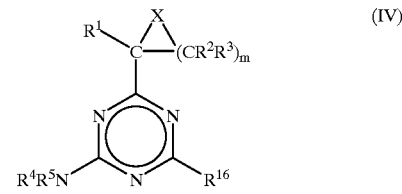

8 Claims, No Drawings

2-AMINO-1,3,5-TRIAZINES, AND THEIR USE AS HERBICIDES AND PLANT GROWTH REGULATORS

The invention relates to the technical field of herbicides and plant growth regulators, especially herbicides for the selective control of broad-leaved and gramineous weeds in crops of useful plants.

It is known that 2-amino-4-alkylamino-6-α-haloalkyl-1,3,5-triazines possess herbicidal and plant growth-regulating properties (WO 90/09378 (EP-A-411153), WO 88/02368 (EP-A-283522), WO 94/24086, EP-A-509544, EP-A-492 615). The use of many of the known derivatives of this type as selective herbicides for weed control or as plant growth regulators in various crops often leads, however, to unwanted damage to the crop plants. Surprisingly, novel 2-amino-1,3,5-triazines have now been found which can be employed with advantage as herbicides and plant growth regulators. When using the compounds according to the invention, for example, the crop plants are undamaged or are not damaged to the same extent as in the case of the known active compounds of similar type.

The present invention provides compounds of the formula (I) and salts thereof

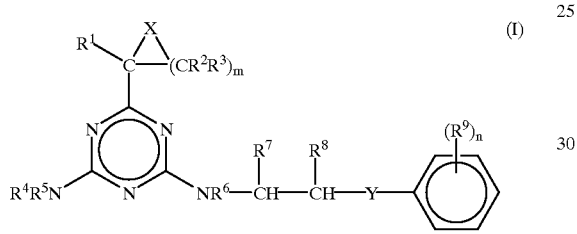

in which $R^1$ is hydrogen, halogen, nitro, cyano, thiocyanato or a radical of the formula $-Z^1-R^{10}$, $R^2$ and $R^3$ in each case independently of one another are hydrogen, halogen, nitro, cyano, thiocyanato or a radical of the formula $-Z^2-R^{11}$, or $R^2$ and $R^3$, together with the carbon atom of the group $CR^2R^3$, are a carbocyclic radical having 4 to 10 ring members or a heterocyclic radical having 4 to 10 ring members and hetero-ring atoms from the group consisting of N, O and S, each of the two latter radicals being unsubstituted or substituted by one or more radicals from the group consisting of halogen, $(C_1-C_4)$alkyl and oxo, $R^4$ and $R^5$ in each case independently of one another are hydrogen, amino, alkylamino or dialkylamino having in each case 1 to 6 carbon atoms in the alkyl radical, an acyclic or cyclic hydrocarbon radical or hydrocarbonoxy radical having in each case 1 to 10 carbon atoms, preferably having 1 to 6 carbon atoms, or a heterocyclyl radical, heterocyclyloxy radical or heterocyclylamino radical having in each case 3 to 6 ring atoms and 1 to 3 hetero-ring atoms from the group consisting of N, O and S, each of the five latter radicals being unsubstituted or substituted, or an acyl radical, or $R^4$ and $R^5$, together with the nitrogen atom of the group $NR^4R^5$, are a heterocyclic radical having 3 to 6 ring atoms and 1 to 4 hetero-ring atoms, any further hetero-ring atoms in addition to the N atom being selected from the group consisting of N, O and S, and the radical being unsubstituted or substituted, $R^6$ is hydrogen, amino, alkylamino or dialkylamino having in each case 1 to 6 carbon atoms in the alkyl radical, an acyclic or cyclic hydrocarbon radical or hydrocarbonoxy radical having in each case 1 to 10 carbon atoms, preferably having 1 to 6 carbon atoms, or a heterocyclyl radical, heterocyclyloxy radical or heterocyclylamino radical having in each case 3 to 6 ring atoms and 1 to 3 hetero-ring atoms from the group consisting of N, O and S, each of the five latter radicals being unsubstituted or substituted, or an acyl radical, $R^7$ and $R^8$ in each case independently of one another are hydrogen, halogen, nitro, cyano, thiocyanato or a radical of the formula $-Z^3-R^{12}$, or $R^7$ and $R^8$ together are an alkylene chain having 2 to 6 carbon atoms which is unsubstituted or substituted by one or more radicals from the group consisting of halogen, $(C_1-C_4)$alkyl and oxo, $R^9$ independently at each occurrence is halogen, nitro, formyl, carboxyl, cyano, thiocyanato, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_4)$alkylcarbonyl, $(C_1-C_4)$alkyloxycarbonyl, $(C_1-C_4)$alkoxy-thiocarbonyl, $(C_1-C_4)$alkylthio-carbonyl or $(C_1-C_4)$alkylthio-thiocarbonyl, the alkyl radicals in the 11 latter radicals being unsubstituted or substituted, or $(C_1-C_4)$alkylsulfonyl, $(C_1-C_4)$haloalkylsulfonyl, $(C_1-C_4)$alkoxysulfonyl, amino, mono- or di-$[(C_1-C_6)$alkyl$]$amino, aminocarbonyl, mono- or di-$[(C_1-C_6)$alkyl$]$aminocarbonyl, $(C_1-C_6)$alkanoylamino, N—$(C_1-C_6)$alkanoyl-N—$(C_1-C_4)$alkyl-amino or a radical of the formula $Z^4-R^o$, in which $Z^4$ is as defined below and $R^o$ is an aromatic, saturated or partially saturated carbocyclic or heterocyclic radical, the cyclic radical being substituted or unsubstituted, or two adjacent radicals $R^9$ together are a fused-on ring having 4 to 6 ring atoms, which is carbocyclic or comprises hetero-ring atoms from the group consisting of O, S and N, and which is unsubstituted or substituted by one or more radicals from the group consisting of halogen, $(C_1-C_4)$alkyl and oxo, $R^{10}$, $R^{11}$, $R^{12}$ in each case independently of one another are H or an acyclic hydrocarbon radical, for example in each case having 1 to 20 carbon atoms, preferably having 1 to 10, or a cyclic hydrocarbon radical, preferably having 3 to 8 carbon atoms, in particular 3 to 6 carbon atoms, or a heterocyclic radical, preferably having 3 to 9 ring atoms and 1 to 3 hetero-ring atoms from the group consisting of N, O and S, each of the three latter radicals being unsubstituted or substituted, X is a group of the formula $-O-$, $-S(O)_q-$, $-NR^*-$ or $-N(O)-$, in which q is 0, 1 or 2 and $R^*$ is hydrogen or alkyl having 1 to 4 carbon atoms, or a group of the formula $CR^{13}R^{14}$ in which the definitions of $R^{13}$ and $R^{14}$ are selected from the radicals possible for $R^2$ and $R^3$, Y is a direct bond or a group of the formula $-O-$, $-S(O)_r-$, $-NR^{}-$ or $-N(O)-$, in which r is 0, 1 or 2 and $R^{}$ is hydrogen or alkyl having 1 to 4 carbon atoms, or a group of the formula $-CH_2-$, $-C(CH_3)H-$ or $-C(CH_3)_2-$, $Z^1$, $Z^2$, $Z^3$ and $Z^4$ in each case independently of one another are a direct bond or a divalent group of the formula $-O-$, $-S(O)_p-$, $-S(O)_p-O-$, $-O-S(O)_p-$, $-CO-$, $-O-CO-$, $-CO-O-$, $-NR'-$, $-O-NR'-$, $-NR'-O-$, $-NR'-CO-$, $-CO-NR'-$ in which p is 0, 1 or 2 and R' is hydrogen, alkyl having 1 to 6 carbon atoms, phenyl, benzyl, cycloalkyl having 3 to 6 carbon atoms or alkanoyl having 1 to 6 carbon atoms, m is 1, 2, 3 or 4, especially 1 or 2, and n is 0, 1, 2, 3, 4 or 5, preferably 0, 1, 2, 3 or 4, especially 2 or 3.

The compounds of the formula (I) can form salts by adding on an appropriate inorganic or organic acid, for example HCl, HBr, $H_2SO_4$ or $HNO_3$, or else oxalic acid or sulfonic acids, to a basic group, for example amino or alkylamino. Suitable substituents, which may be in deprotonated form, such as, for example, sulfonic acids or carboxylic acids, may form inner salts with groups which are in turn protonatable, such as amino groups. Salts can likewise be formed by replacing the hydrogen in appropriate substituents, for example sulfonic acids or carboxylic acids, by an agriculturally appropriate cation. Examples of these salts are metal salts, especially alkali metal salts, or alkaline earth metal salts, in particular sodium salts and potassium salts, or else ammonium salts or salts with organic amines.

In formula (I) and all subsequent formulae the radicals alkyl, alkoxy, haloalkyl, haloalkoxy, alkylamino and alkylthio and the corresponding unsaturated and/or substituted radicals can in each case be straight-chain or branched within the carbon framework. Unless indicated specifically, the lower carbon frameworks of these radicals are preferred, for example having 1 to 6 carbon atoms or, in the case of unsaturated groups, having 2 to 6 carbon atoms. Alkyl radicals, both alone and in the composite meanings, such as alkoxy, haloalkyl, etc., are for example methyl, ethyl, n- or isopropyl, n-, iso-, t- or 2-butyl, pentyls, hexyls, such as n-hexyl, iso-hexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals; alkenyl is for example allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is for example propargyl, but-2-yn-1-yl, but-3-yn-1-yl, 1-methyl-but-3-yn-1-yl.

Cycloalkyl is a carbocyclic saturated ring system having preferably 3–8 carbon atoms, for example cyclopropyl, cyclopentyl or cyclohexyl.

Halogen is for example fluorine, chlorine, bromine or iodine. Haloalkyl, -alkenyl and -alkynyl are, respectively, alkyl, alkenyl and alkynyl substituted completely or partially by halogen, preferably by fluorine, chlorine and/or bromine, especially by fluorine or chlorine, examples being monohaloalkyl (=mono-halogenalkyl), perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF_3CF_2O$, $OCH_2CF_3$ and $OCH_2CH_2Cl$; similar comments apply to haloalkenyl and other halogen-substituted radicals.

A hydrocarbon radical is a straight-chain, branched or cyclic and saturated or unsaturated, aliphatic or aromatic hydrocarbon radical, for example alkyl, alkenyl, alkynyl, cycloalkyl, cycloalkenyl or aryl; aryl in this case is a mono-, bi- or polycyclic aromatic system, for example phenyl, naphthyl, tetrahydronaphthyl, indenyl, indanyl, pentalenyl, fluorenyl and the like, preferably phenyl;

a hydrocarbon radical is preferably alkyl, alkenyl or alkynyl having up to 12 carbon atoms or cycloalkyl having 3, 4, 5, 6 or 7 ring atoms or phenyl; similar comments apply to a hydrocarbon radical in a hydrocarbonoxy radical.

A heterocyclic radical or ring (heterocyclyl) can be saturated, unsaturated or heteroaromatic; it preferably contains one or more hetero-units in the ring, i.e. heteroatoms or ring members which also include substituted heteroatoms, preferably from the group consisting of N, O, S , SO and $SO_2$; it is preferably an aliphatic heterocyclyl radical having 3 to 7 ring atoms or a heteroaromatic radical having 5 or 6 ring atoms and contains 1, 2 or 3 hetero-units. The heterocyclic radical can for example be a heteroaromatic radical or ring (heteroaryl), for example a mono-, bi- or polycyclic aromatic system, in which at least 1 ring comprises one or more heteroatoms, examples being pyridyl, pyrimidinyl, pyridazinyl, pyrazinyl, thienyl, thiazolyl, oxazolyl, furyl, pyrrolyl, pyrazolyl and imidazolyl, or is a partially or completely hydrogenated radical such as oxiranyl, pyrrolidyl, piperidyl, piperazinyl, dioxolanyl, morpholinyl and tetrahydrofuryl. Suitable substituents of a substituted heterocyclic radical are those mentioned further below, and also oxo. The oxo group can also occur at the hetero-ring atoms, which may exist in various oxidation stages, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are for example a substituted radical which is derived from the unsubstituted parent structure, the substituents being, for example, one or more radicals, preferably 1, 2 or 3 radicals, from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl; in the term "substituted radicals" such as substituted alkyl etc., substituents include not only the abovementioned saturated hydrocarbon-containing radicals but also the corresponding unsaturated aliphatic and aromatic radicals, such as substituted or unsubstituted alkenyl, alkynyl, alkenyloxy, alkynyloxy, phenyl, phenoxy, etc. In the case of radicals containing carbon atoms, preference is given to those having 1 to 4 carbon atoms, especially 1 or 2 carbon atoms. Generally preferred substituents are those from the group consisting of halogen, for example fluorine and chlorine, $(C_1-C_4)$alkyl, preferably methyl and ethyl, $(C_1-C_4)$haloalkyl, preferably trifluoromethyl, $(C_1-C_4)$alkoxy, preferably methoxy and ethoxy, and $(C_1-C_4)$haloalkoxy, nitro and cyano. Particularly preferred in this context are the substituents methyl, methoxy and chlorine.

Mono- or disubstituted amino is a chemically stable radical from the group consisting of the substituted amino radicals which are N-substituted, for example, by one or two identical or different radicals from the group consisting of alkyl, alkoxy, acyl and aryl; they are preferably monoalkylamino, dialkylamino, acylamino, arylamino, N-alkyl-N-arylamino and N-heterocycles; in this context alkyl radicals having 1 to 4 carbon atoms are preferred, aryl is preferably phenyl or substituted phenyl, and acyl is subject to the definition given further below, and is preferably $(C_1-C_4)$alkanoyl. Similar comments apply to substituted hydroxylamino or hydrazino.

Substituted or unsubstituted phenyl is preferably phenyl which is unsubstituted or is substituted one or more times, preferably up to three times, by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl and o-, m- and p-methoxyphenyl.

An acyl radical is the radical of an organic acid, for example the radical of a carboxylic acid and radicals of acids derived therefrom, such as of thiocarboxylic acid, unsubstituted or N-substituted iminocarboxylic acids or the radical of carbonic monoesters, unsubstituted or N-substituted carbamic acid, sulfonic acids, sulfinic acids, phosphonic acids and phosphinic acids. Acyl is for example formyl, alkylcarbonyl such as [($C_1$–$C_4$)alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. These radicals can in each case be substituted further in the alkyl or phenyl moiety, for example in the alkyl moiety by one or more radicals from the group consisting of halogen, alkoxy, phenyl and phenoxy; examples of substituents in the phenyl moiety are the substituents already mentioned further above in general for substituted phenyl.

The invention also provides all stereoisomers covered by formula (I), and mixtures thereof. Such compounds of the formula (I) contain one or more asymmetric carbon atoms or else double bonds, which are not indicated separately in the general formulae (I). The possible stereoisomers defined by their specific spatial form, such as enantiomers, diastereomers, Z and E isomers, are all covered by the formula (I) and can be obtained by customary methods from mixtures of the stereoisomers or else by stereoselective reactions in combination with the use of stereochemically pure starting materials.

For reasons in particular of greater herbicidal action, better selectivity and/or greater ease of preparation, particular interest attaches to novel compounds of the abovementioned formula (I) or salts thereof in which $R^1$ is H, halogen, $NO_2$, CN, SCN or —$Z^1$—$R^{10}$, $R^2$ and $R^3$ in each case independently of one another are
H, halogen, $NO_2$, CN, SCN or a radical of the formula
—$Z^2$—$R^{11}$ or $R^2$ and $R^3$, together with the carbon atom of the group $CR^2R^3$, are ($C_3$–$C_8$)cycloalkyl, ($C_3$–$C_8$)cycloalkenyl or a heterocyclic radical having 3 to 6 ring members and having hetero-ring atoms from the group consisting of N, O and S, each of the 3 latter radicals being unsubstituted or substituted by one or more radicals from the group consisting of halogen, ($C_1$–$C_4$)alkyl and oxo, $R^4$ and $R^5$ in each case independently of one another are
hydrogen, amino, alkylamino or dialkylamino having in each case 1 to 4 carbon atoms in the alkyl radical, an acyclic or cyclic hydrocarbon radical or hydrocarbonoxy radical having in each case 1 to 6 carbon atoms or a heterocyclyl radical, heterocyclyloxy radical or heterocyclylamino radical having in each case 3 to 6 ring atoms and 1 to 3 hetero-ring atoms from the group consisting of N, O and S, each of the five latter radicals being unsubstituted or substituted by one or more radicals from the group consisting of halogen, ($C_1$–$C_4$) alkoxy, ($C_1$–$C_4$)haloalkoxy, ($C_1$–$C_4$)alkylthio, ($C_2$–$C_4$) alkenyl, ($C_2$–$C_4$)alkynyl, ($C_2$–$C_4$)alkenyloxy, ($C_2$–$C_4$) alkynyloxy, hydroxyl, amino, acylamino, mono- and dialkylamino, nitro, carboxyl, cyano, azido, [($C_1$–$C_4$) alkoxy]-carbonyl, [($C_1$–$C_4$)alkyl]-carbonyl, formyl, carbamoyl, mono- and di-[($C_1$–$C_4$)alkyl]-aminocarbonyl, ($C_1$–$C_4$)alkylsulfinyl, ($C_1$–$C_4$) haloalkylsulfinyl, ($C_1$–$C_4$)alkylsulfonyl, ($C_1$–$C_4$) haloalkylsulfonyl and, in the case of cyclic radicals, also ($C_1$–$C_4$)alkyl and ($C_1$–$C_4$)haloalkyl, or an acyl radical, or $R^4$ and $R^5$, together with the nitrogen atom of the group $NR^4R^5$, are a heterocyclic radical having 3 to 6 ring atoms and 1 to 2 hetero-ring atoms, any further hetero-ring atom in addition to the N atom being selected from the group consisting of N, O and S and the radical being unsubstituted or substituted by one or more radicals from the group consisting of halogen, ($C_1$–$C_4$)alkyl and oxo, $R^6$ is hydrogen, amino, alkylamino or dialkylamino having in each case 1 to 6 carbon atoms in the alkyl radical, an acyclic or cyclic hydrocarbon radical or hydrocarbonoxy radical having in each case 1 to 6 carbon atoms or a heterocyclyl radical, heterocyclyloxy radical or heterocyclylamino radical having in each case 3 to 6 ring atoms and 1 to 3 hetero-ring atoms from the group consisting of N, O and S, each of the five latter radicals being unsubstituted or substituted by one or more radicals from the group consisting of halogen, ($C_1$–$C_4$) alkoxy, ($C_1$–$C_4$)haloalkoxy, ($C_1$–$C_4$)alkylthio, ($C_2$–$C_4$) alkenyl, ($C_2$–$C_4$)alkynyl, ($C_2$–$C_4$)alkenyloxy, ($C_2$–$C_4$) alkynyloxy, hydroxyl, amino, acylamino, mono- and dialkylamino, nitro, carboxyl, cyano, azido, [($C_1$–$C_4$) alkoxy]-carbonyl, [($C_1$–$C_4$)alkyl]-carbonyl, formyl, carbamoyl, mono- and di-[($C_1$–$C_4$)alkyl]-aminocarbonyl, ($C_1$–$C_4$)alkylsulfinyl, ($C_1$–$C_4$) haloalkylsulfinyl, ($C_1$–$C_4$)alkylsulfonyl, ($C_1$–$C_4$) haloalkylsulfonyl and, in the case of cyclic radicals, also ($C_1$–$C_4$)alkyl and ($C_1$–$C_4$)haloalkyl, or an acyl radical, $R^7$ and $R^8$ in each case independently of one another are H, halogen, $NO_2$, CN, SCN or a radical of the formula —$Z^3$—$R^{12}$ or $R^7$ and $R^8$ together are an alkylene chain having 2 to 4 carbon atoms which is unsubstituted or substituted by one or more radicals from the group consisting of halogen, ($C_1$–$C_4$)alkyl and oxo, $R^9$ independently at each occurrence is halogen, nitro, formyl, carboxyl, cyano, thiocyanato, ($C_1$–$C_6$)alkyl, ($C_1$–$C_6$)alkoxy, ($C_1$–$C_4$)alkylcarbonyl, ($C_1$–$C_4$) alkyloxycarbonyl or ($C_1$–$C_4$)alkylthiocarbonyl, the five latter radicals being unsubstituted or substituted by halogen or ($C_1$–$C_4$)alkoxy, or ($C_1$–$C_4$)alkylsulfonyl, ($C_1$–$C_4$)haloalkylsulfonyl, mono- or di-[($C_1$–$C_4$)alkyl] amino, aminocarbonyl, mono- or di-[($C_1$–$C_4$)alkyl] aminocarbonyl, ($C_1$–$C_4$)alkanoylamino or a radical of the formula $Z^4$—$R^o$, in which $Z^4$ is as defined below and $R^o$ is ($C_3$–$C_6$)cycloalkyl, ($C_3$–$C_6$)cycloalkenyl or phenyl, each of the three latter radicals being unsubstituted or substituted by radicals from the group consisting of halogen, ($C_1$–$C_4$)alkyl, ($C_1$–$C_4$)haloalkyl and ($C_1$–$C_4$)alkoxy, or two adjacent radicals $R^9$ together are a fused-on ring having 4 to 6 ring atoms, which is carbocyclic or comprises hetero-ring atoms from the group consisting of O, S and N, and which is unsubstituted or substituted by one or more radicals from the group consisting of halogen, ($C_1$–$C_4$)alkyl and oxo, $R^{10}$, $R^{11}$ and $R^{12}$ in each case independently of one another are H or an acyclic hydrocarbon radical having 1 to 6 carbon atoms, a cyclic hydrocarbon radical having 3 to 6 carbon atoms or a heterocyclic radical having 3 to 9 ring atoms and 1 to 3 hetero-ring atoms from the group consisting of N, O and S, each of the three latter radicals being unsubstituted or substituted by one or more radicals from the group consisting of halogen, ($C_1$–$C_4$)alkoxy, ($C_1$–$C_4$)haloalkoxy, ($C_1$–$C_4$) alkylthio, ($C_2$–$C_4$)alkenyl, ($C_2$–$C_4$)alkynyl, ($C_2$–$C_4$) alkenyloxy, ($C_2$–$C_4$)alkynyloxy, hydroxyl, amino, acylamino, mono- and dialkylamino, nitro, carboxyl, cyano, azido, [($C_1$–$C_4$)alkoxy]-carbonyl, [($C_1$–$C_4$)

alkyl]-carbonyl, formyl, carbamoyl, mono- and di-[($C_1$–$C_4$)alkyl]-aminocarbonyl, ($C_1$–$C_4$)alkylsulfinyl, ($C_1$–$C_4$)haloalkylsulfinyl, ($C_1$–$C_4$)alkylsulfonyl, ($C_1$–$C_4$)haloalkylsulfonyl and, in the case of cyclic radicals, also ($C_1$–$C_4$)alkyl and ($C_1$–$C_4$)haloalkyl, preferably, $R^{10}$, $R^{11}$ and $R^{12}$ are hydrogen, ($C_1$–$C_8$) alkyl, ($C_2$–$C_6$)alkenyl, ($C_2$–$C_6$)alkynyl, ($C_3$–$C_9$) cycloalkyl, ($C_3$–$C_9$)cycloalkenyl, phenyl, heterocyclyl having 3 to 6 ring atoms and 1 to 3 hetero-ring atoms from the group consisting of N, O and S, each of the 7 latter radicals being unsubstituted or substituted by one or more radicals from the group consisting of halogen, ($C_1$–$C_4$)alkoxy, ($C_1$–$C_4$)haloalkoxy, ($C_1$–$C_4$)alkylthio, amino, mono- and di[($C_1$–$C_4$)alkyl]amino, ($C_1$–$C_4$) alkanoylamino, benzoylamino, nitro, cyano, [($C_1$–$C_4$) alkyl]carbonyl, formyl, carbamoyl, mono- and di-[($C_1$–$C_4$)alkyl]aminocarbonyl, ($C_1$–$C_4$)alkylsulfonyl and, in the case of cyclic radicals, also ($C_1$–$C_4$)alkyl and ($C_1$–$C_4$)haloalkyl, X is a group of the formula —O—, —S(O)$_q$—, —NR*— or —N(O)—, in which q is 0, 1 or 2 and R* is hydrogen or alkyl having 1 to 4 carbon atoms, or a group of the formula $CR^{13}R^{14}$ in which the definitions of $R^{13}$ and $R^{14}$ are selected from the radicals possible for $R^2$ and $R^3$, Y is a direct bond or a group of the formula —O—, —S(O)$_r$—, —NR— or —N(O)—, in which r is 0, 1 or 2 and R is hydrogen or alkyl having 1 to 4 carbon atoms, or a group of the formula —$CH_2$—, —$C(CH_3)$H— or —$C(CH_3)_2$—, $Z^1$, $Z^2$, $Z^3$ and $Z^4$ in each case independently of one another are a direct bond or a divalent group of the formula —O—, —S—, —CO—, —O—CO—, —CO—O—, —NR'—, —NR'—CO— or —CO—NR'—, in which R' is H or ($C_1$–$C_4$)alkyl; preferably $Z^1$, $Z^2$, $Z^3$ and $Z^4$ are a direct bond or oxygen.

Of particular interest, furthermore, are novel compounds of the formula (I) and salts thereof in which $R^1$, $R^2$ and $R^3$ independently of one another are hydrogen, halogen, hydroxyl, amino, nitro, formyl, carboxyl, cyano, thiocyanato, ($C_1$–$C_4$)alkyl, cyano-($C_1$–$C_4$)alkyl, ($C_1$–$C_4$)alkoxy, ($C_1$–$C_4$)alkylamino, di-[($C_1$–$C_4$)alkyl]-amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_1$–$C_4$)alkylthio, halo-($C_1$–$C_4$) alkylthio, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$) alkylamino-($C_1$–$C_4$)alkyl, di-[($C_1$–$C_4$)alkyl]-amino-($C_1$–$C_4$)alkyl, ($C_3$–$C_9$)cycloalkylamino-($C_1$–$C_4$)alkyl, ($C_3$–$C_9$)cycloalkyl, heterocyclyl-($C_1$–$C_4$)alkyl having 3 to 9 ring members, the cyclic groups in the 3 latter radicals being unsubstituted or substituted by one or more radicals, preferably up to three radicals, from the group consisting of ($C_1$–$C_4$)alkyl, halogen and cyano, or phenyl, phenoxy, phenylcarbonyl, phenylcarbonyl-($C_1$–$C_4$)alkyl, ($C_1$–$C_4$)alkoxy-carbonyl-($C_1$–$C_4$) alkyl, ($C_1$–$C_4$)alkylamino-carbonyl-($C_1$–$C_4$)alkyl, ($C_1$–$C_4$)alkyl-carbonyl, ($C_1$–$C_4$)alkoxy-carbonyl, aminocarbonyl, ($C_1$–$C_4$)alkylamino-carbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the 16 latter radicals which is substituted in the acyclic moiety or, preferably, in the cyclic moiety by one or more radicals from the group consisting of halogen, nitro, cyano, ($C_1$–$C_4$)alkyl, ($C_1$–$C_4$)alkoxy, ($C_1$–$C_4$) alkylthio, ($C_1$–$C_4$)haloalkyl, ($C_1$–$C_4$)haloalkoxy, formyl, ($C_1$–$C_4$)alkyl-carbonyl, ($C_1$–$C_4$)alkoxy-carbonyl and ($C_1$–$C_4$)alkoxy, heterocyclyl in the radicals containing in each case 3 to 9 ring atoms and 1 to 3 hetero-ring atoms from the group consisting of N, O and S, or $R^2$ and $R^3$ together with the carbon atom of the group $CR^2R^3$, are a saturated or partially unsaturated carbocyclic radical having 3 to 6 ring members or heterocyclyl having 3 to 6 ring members and 1 to 3 hetero-ring atoms from the group consisting of O, N and S, each of the 2 latter cyclic radicals being unsubstituted or substituted by one or more radicals from the group consisting of ($C_1$–$C_4$)alkyl, halogen and oxo, $R^4$ and $R^5$ independently of one another are hydrogen, amino, formyl, ($C_1$–$C_4$)alkyl, cyano-($C_1$–$C_4$)alkyl, ($C_1$–$C_4$)alkylamino, di-[($C_1$–$C_4$)alkyl]-amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$) alkyl, di-[($C_1$–$C_4$)alkyl]-amino-($C_1$–$C_4$)alkyl, ($C_3$–$C_9$) cycloalkylamino-($C_1$–$C_4$)alkyl, ($C_3$–$C_9$)cycloalkyl, ($C_3$–$C_9$)heterocyclyl-($C_1$–$C_4$)alkyl having 3 to 9 ring members, the cyclic groups in the 3 latter radicals being unsubstituted or substituted by one or more radicals, preferably up to three radicals, from the group consisting of ($C_1$–$C_4$)alkyl, halogen and cyano, or phenyl, phenoxy, phenylcarbonyl, phenylcarbonyl-($C_1$–$C_4$)alkyl, ($C_1$–$C_4$)alkoxy-carbonyl-($C_1$–$C_4$) alkyl, ($C_1$–$C_4$)alkylamino-carbonyl-($C_1$–$C_4$)alkyl, ($C_1$–$C_4$)alkyl-carbonyl, ($C_1$–$C_4$)alkoxy-carbonyl, aminocarbonyl, ($C_1$–$C_4$)alkylamino-carbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the 16 latter radicals which is substituted in the acyclic moiety or, preferably in the cyclic moiety by one or more radicals from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkyl-carbonyl, ($C_1$–$C_4$)alkoxy-carbonyl and ($C_1$–$C_4$)alkoxy, heterocyclyl in the radicals containing in each case 3 to 9 ring atoms and 1 to 3 hetero-ring atoms from the group consisting of N, O and S, or $R^4$ and $R^5$, together with the nitrogen atom of the group $NR^4R^5$, are a heterocyclic radical having 3 to 6 ring atoms and 1 to 2 hetero-ring atoms, any further hetero-ring atom in addition to the N atom being selected from the group consisting of N, O and S, and the radical being unsubstituted or substituted by one or more radicals from the group consisting of halogen, ($C_1$–$C_4$)alkyl and oxo, $R^6$ is hydrogen, amino, formyl, ($C_1$–$C_4$)alkyl, cyano-($C_1$–$C_4$)alkyl, ($C_1$–$C_4$)alkylamino, di-[($C_1$–$C_4$)alkyl]-amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$) alkylamino-($C_1$–$C_4$)alkyl, di-[($C_1$–$C_4$)alkyl]-amino-($C_1$–$C_4$)alkyl, ($C_3$–$C_9$)cycloalkylamino-($C_1$–$C_4$)alkyl, ($C_3$–$C_9$)cycloalkyl, ($C_3$–$C_9$)heterocyclyl-($C_1$–$C_4$)alkyl having 3 to 9 ring members, the cyclic groups in the 3 latter radicals being unsubstituted or substituted by one or more radicals, preferably up to three radicals, from the group consisting of ($C_1$–$C_4$)alkyl, halogen and cyano, or phenyl, phenoxy, phenylcarbonyl, phenylcarbonyl-($C_1$–$C_4$)alkyl, ($C_1$–$C_4$)alkoxy-carbonyl-($C_1$–$C_4$)alkyl, ($C_1$–$C_4$)alkylamino-carbonyl-($C_1$–$C_4$)alkyl, ($C_1$–$C_4$)alkyl-carbonyl, ($C_1$–$C_4$)alkoxy-carbonyl, aminocarbonyl, ($C_1$–$C_4$)alkylamino-carbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the 16 latter radicals which is substituted in the acyclic moiety or, preferably, in the cyclic moiety by one or more radicals from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkyl-carbonyl, ($C_1$–$C_4$)alkoxy-carbonyl and ($C_1$–$C_4$)alkoxy, heterocyclyl in the radicals containing in each case 3 to 9 ring atoms and 1 to 3 hetero-ring atoms from the group consisting of N, O and S, or $R^7$ and $R^8$ independently of one another are hydrogen, halogen, hydroxyl, amino, nitro, formyl, carboxyl, cyano, thiocyanato, ($C_1$–$C_4$)alkyl, cyano-($C_1$–$C_4$)alkyl, ($C_1$–$C_4$)alkoxy, ($C_1$–$C_4$)alkylamino, di-[($C_1$–$C_4$)alkyl]-amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_1$–$C_4$)alkylthio, halo-($C_1$–$C_4$)alkylthio, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$)alkyl, di-[($C_1$–$C_4$)alkyl]-amino-($C_1$–$C_4$)alkyl, ($C_3$–$C_9$)cycloalkylamino-($C_1$–$C_4$)alkyl, ($C_3$–$C_9$)cycloalkyl, heterocyclyl-($C_1$–$C_4$)alkyl having 3 to 9 ring members, the cyclic groups in the 3 latter radicals being unsubstituted or substituted by one or more radicals, preferably up to three radicals, from the group consisting of ($C_1$–$C_4$)alkyl, halogen and cyano, or phenyl, phenoxy, phenylcarbonyl, phenylcarbonyl-($C_1$–$C_4$)alkyl, ($C_1$–$C_4$)alkoxy-carbonyl-($C_1$–$C_4$)alkyl, ($C_1$–$C_4$)alkylamino-carbonyl-($C_1$–$C_4$)alkyl, ($C_1$–$C_4$)alkyl-carbonyl, ($C_1$–$C_4$)alkoxy-carbonyl, aminocarbonyl, ($C_1$–$C_4$)alkylamino-carbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the 16 latter radicals which is substituted in the acyclic moiety or, preferably, in the cyclic moiety by one or more radicals from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkyl-carbonyl, ($C_1$–$C_4$)alkoxy-carbonyl and ($C_1$–$C_4$)alkoxy, heterocyclyl in the radicals containing in each case 3 to 9 ring atoms and 1 to 3 hetero-ring atoms from the group consisting of N, O and S, or $R^7$ and $R^8$ together are an alkylene chain having 2 to 4 carbon atoms, which is unsubstituted or substituted by one or more radicals from the group consisting of halogen, ($C_1$–$C_4$)alkyl and oxo, $R^9$, if n is 1, and the radicals $R^9$, independently at each occurrence, if n is greater than 1, is or are hydrogen, halogen, hydroxyl, amino, nitro, formyl, carboxyl, cyano, thiocyanato, ($C_1$–$C_4$)alkyl, cyano-($C_1$–$C_4$)alkyl, ($C_1$–$C_4$)alkoxy, ($C_1$–$C_4$)alkylamino, di-[($C_1$–$C_4$)alkyl]-amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_1$–$C_4$)alkylthio, halo-($C_1$–$C_4$)alkylthio, ($C_2$–$C_6$)alkenyl, halo-($C_2$–$C_6$)alkenyl, ($C_2$–$C_6$)alkynyl, halo-($C_2$–$C_6$)alkinyl, ($C_1$–$C_4$)alkylamino-($C_1$–$C_4$)alkyl, di-[($C_1$–$C_4$)alkyl]-amino-($C_1$–$C_4$)alkyl, ($C_3$–$C_9$)cycloalkylamino-($C_1$–$C_4$)alkyl, ($C_3$–$C_9$)cycloalkyl, heterocyclyl-($C_1$–$C_4$)alkyl having 3 to 9 ring members, the cyclic groups in the 3 latter radicals being unsubstituted or substituted by one or more radicals, preferably up to three radicals, from the group consisting of ($C_1$–$C_4$)alkyl, halogen and cyano, or phenyl, phenoxy, phenylcarbonyl, phenylcarbonyl-($C_1$–$C_4$)alkyl, ($C_1$–$C_4$)alkoxy-carbonyl-($C_1$–$C_4$)alkyl, ($C_1$–$C_4$)alkylamino-carbonyl-($C_1$$C_4$)alkyl, ($C_1$–$C_4$)alkyl-carbonyl, ($C_1$–$C_4$)alkoxy-carbonyl, aminocarbonyl, ($C_1$–$C_4$)alkylamino-carbonyl, phenoxy-($C_1$–$C_4$)alkyl, phenyl-($C_1$–$C_4$)alkyl, heterocyclyl, heterocyclylamino, heterocyclyloxy, heterocyclylthio or one of the 16 latter radicals which is substituted in the acyclic moiety or, preferably, in the cyclic moiety by one or more radicals from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkyl-carbonyl, ($C_1$–$C_4$)alkoxy-carbonyl and ($C_1$–$C_4$)alkoxy, heterocyclyl in the radicals containing in each case 3 to 9 ring atoms and 1 to 3 hetero-ring atoms from the group consisting of N, O and S, or two adjacent radicals $R^9$ together are a fused-on ring having 4 to 6 ring atoms which is carbocyclic or comprises hetero-ring atoms from the group consisting of O, S and N, and which is unsubstituted or substituted by one or more radicals from the group consisting of halogen, ($C_1$–$C_4$)alkyl and oxo, X is a group of the formula —O—, —S— or —NR*—, in which R* is hydrogen or alkyl having 1 to 4 carbon atoms, or a group of the formula $CR^{13}R^{14}$, in which the definitions of $R^{13}$ and $R^{14}$ are selected from the radicals possible for $R^2$ and $R^3$, Y is a direct bond or a group of the formula —O—, —S— or —NR—, in which R is hydrogen or alkyl having 1 to 4 carbon atoms, or a group of the formula —$CH_2$—, —$C(CH_3)H$— or —$C(CH_3)_2$—.

Also of particular interest are novel compounds of the formula (I) and salts thereof in which $R^1$ is hydrogen, halogen, hydroxyl, amino, ($C_1$–$C_4$)alkyl, ($C_1$–$C_4$)alkoxy, ($C_1$–$C_4$)alkylamino, di-[($C_1$–$C_4$)alkyl]-amino, halo-($C_1$–$C_4$)alkyl, ($C_1$–$C_4$)alkoxy-($C_1$–$C_4$)alkyl, ($C_2$–$C_6$)alkenyl, ($C_2$–$C_6$)alkynyl, phenyl, phenoxy or a phenyl or phenoxy radical which is substituted in the phenyl moiety by one or more radicals, preferably up to a total of three radicals, from the group consisting of halogen, ($C_1$–$C_4$)alkyl, ($C_1$–$C_4$)alkoxy and ($C_1$–$C_4$)alkoxy-carbonyl, $R^2$ and $R^3$ independently of one another are hydrogen, halogen, hydroxyl, amino, ($C_1$–$C_4$)alkyl, ($C_1$–$C_4$)alkoxy, ($C_1$–$C_4$)alkylamino, di-[($C_1$–$C_4$)alkyl]-amino, halo-($C_1$–$C_4$)alkyl, ($C_1$–$C_4$)alkoxy-($C_1$–$C_4$)alkyl, ($C_2$–$C_6$)alkenyl, ($C_2$–$C_6$)alkynyl, phenyl or phenoxy or a phenyl or phenoxy radical which is substituted in the phenyl moiety by one or more radicals, preferably up to a total of three radicals, from the group consisting of halogen, ($C_1$–$C_4$)alkyl, ($C_1$–$C_4$)alkoxy and ($C_1$–$C_4$)alkoxy-carbonyl, or $R^2$ and $R^3$, together with the carbon atom of the group $CR^2R^3$, are a saturated carbocyclic radical having 3 to 6 ring members which is unsubstituted or substituted by one or more radicals from the group consisting of ($C_1$–$C_4$)alkyl, halogen and oxo, $R^4$ and $R^5$ independently of one another are hydrogen, amino, formyl, $(C_1-C_4)$alkyl, $(C_1-C_4)$alkoxy-$(C_1-C_4)$alkyl, $(C_2-C_6)$alkenyl, $(C_2-C_6)$alkynyl, $(C_1-C_4)$alkylamino-$(C_1-C_4)$alkyl, di-$[(C_1-C_4)$alkyl]-amino-$(C_1-C_4)$alkyl or phenyl, phenyl-$(C_1-C_4)$alkyl or phenoxy-carbonyl or one of the three latter radicals which is substituted in the phenyl moiety up to three times by radicals from the group consisting of halogen, $(C_1-C_4)$alkyl, $(C_1-C_4)$alkoxy and $(C_1-C_4)$alkoxy-carbonyl, or $R^4$ and $R^5$, together with the nitrogen atom of the group $NR^4R^5$, are a heterocyclic radical having 3 to 6 ring atoms and 1 to 2 hetero-ring atoms, any further hetero-ring atom in addition to the N atom being selected from the group consisting of N and O, and the radical being unsubstituted or substituted by one or more radicals from the group consisting of halogen, $(C_1-C_4)$alkyl and oxo, $R^6$ is hydrogen, amino, formyl, $(C_1-C_4)$alkyl, di-$[(C_1-C_4)$alkyl]-amino, $(C_1-C_4)$alkoxy-$(C_1-C_4)$alkyl, $(C_2-C_6)$alkenyl, $(C_2-C_6)$alkynyl, $(C_1-C_4)$dialkylamino-$(C_1-C_4)$alkyl, phenyl, phenoxy-$(C_1-C_4)$alkyl, phenyl-$(C_1-C_4)$alkyl, phenoxy-carbonyl, phenylaminocarbonyl or one of the five latter radicals which is substituted in the phenyl moiety from one to three times by radicals from the group consisting of halogen, $(C_1-C_4)$alkyl, $(C_1-C_4)$alkoxy and $(C_1-C_4)$alkoxy-carbonyl, $R^7$ and $R^8$ independently of one another are hydrogen, $(C_1-C_4)$alkyl, $(C_1-C_4)$alkoxy-$(C_1-C_4)$alkyl, $(C_2-C_6)$alkenyl, $(C_2-C_6)$alkynyl, di-$[(C_1-C_4)$alkyl]-amino-$(C_1-C_4)$alkyl, phenyl, phenoxy-$(C_1-C_4)$alkyl, phenyl-$(C_1-C_4)$alkyl or one of the three latter radicals, which is substituted in the phenyl moiety from one to three times by radicals from the group consisting of halogen, $(C_1-C_4)$alkyl, $(C_1-C_4)$alkoxy and $(C_1-C_4)$alkoxy-carbonyl, or $R^7$ and $R^8$ together are an alkylene chain having 2 to 4 carbon atoms, which is unsubstituted or substituted by one or more radicals from the group consisting of halogen, $(C_1-C_4)$alkyl and oxo, $R^9$ independently at each occurrence is hydrogen, halogen, hydroxyl, amino, nitro, cyano, $(C_1-C_4)$alkyl, $(C_1-C_4)$alkoxy, $(C_1-C_4)$alkylamino, di-$[(C_1-C_4)$alkyl]-amino, perhalo-$(C_1-C_4)$alkyl, hydroxy-$(C_1-C_4)$alkyl, $(C_1-C_4)$alkoxy-$(C_1-C_4)$alkyl, $(C_1-C_4)$alkylthio, $(C_2-C_6)$alkenyl, $(C_2-C_6)$alkynyl, di-$[(C_1-C_4)$alkyl]-amino-$(C_1-C_4)$alkyl, phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylcarbonyl, $(C_1-C_4)$alkyloxycarbonyl, phenoxy-$(C_1-C_4)$alkyl, phenyl-$(C_1-C_4)$alkyl, heterocyclyl, heterocyclylamino, heterocyclyloxy, heterocyclylthio or one of the 13 latter radicals which is substituted in the acyclic moiety or, preferably, in the cyclic moiety by one or more radicals from the group consisting of halogen, $(C_1-C_4)$alkyl, $(C_1-C_4)$alkoxy, $(C_1-C_4)$alkylthio, $(C_1-C_4)$haloalkyl, $(C_1-C_4)$haloalkoxy and $(C_1-C_4)$alkoxy-carbonyl, heterocyclyl in the radicals having 3 to 6 ring atoms and 1 to 3 hetero-ring atoms from the group consisting of N and O, or two adjacent radicals $R^9$ together are a fused-on ring having 4 to 6 ring atoms which is carbocyclic or comprises hetero-ring atoms from the group consisting of O and N, and which is unsubstituted or substituted by one or more $(C_1-C_4)$alkyl radicals, X is a group of the formula —O— or —NR*—, in which R* is hydrogen or methyl, or a group of the formula $CR^{13}R^{14}$, in which the definitions of $R^{13}$ and $R^{14}$ are selected from the radicals possible for $R^2$ and $R^3$, Y is a direct bond or a group of the formula —O— or —NR—, in which R is hydrogen or methyl.

Preferred novel compounds of the formula (I) and salts thereof are those in which $R^1$ is hydrogen, halogen or $(C_1-C_4)$alkyl, $R^2$ and $R^3$ independently of one another are hydrogen, halogen, $(C_1-C_4)$alkyl or phenyl or $R^2$ and $R^3$ together with the carbon atom of the group $CR^2R^3$, are saturated $(C_4-C_6)$cycloalkyl, $R^4$ and $R^5$ independently of one another are hydrogen, amino, formyl or $(C_1-C_4)$alkyl, or $R^4$ and $R^5$ together with the nitrogen atom of the group $NR^4R^5$, are a heterocyclic radical having 4 to 6 ring atoms and 1 to 2 hetero-ring atoms, any further hetero-ring atom in addition to the N atom being selected from the group consisting of N and O, $R^6$ is hydrogen or $(C_1-C_4)$alkyl, $R^7$ and $R^8$ independently of one another are hydrogen, $(C_1-C_4)$alkyl or $(C_1-C_4)$alkoxy-$(C_1-C_4)$alkyl or $R^7$ and $R^8$ together are an alkylene chain having 2 to 4 carbon atoms, $R^9$ independently at each occurrence is hydrogen, halogen, hydroxyl, $(C_1-C_4)$alkyl or $(C_1-C_4)$alkoxy, m is 1 or 2, n is 2 or 3, X is a group of the formula —O— or —NH—, or a group of the formula $CR^{13}R^{14}$, in which the definitions of $R^{13}$ and $R^{14}$ are selected from the radicals possible for $R^2$ and $R^3$, Y is a direct bond or a group of the formula —O— or —NH—.

The present invention also provides processes for the preparation of the compounds of the formula (I) or salts thereof, which comprise a) reacting a compound of the formula (II),

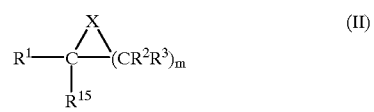

in which $R^{15}$ is a functional group from the group consisting of carboxylate, carboxylic acid ortho ester, carbonyl chloride, carboxamide, carboxylic anhydride and trichloromethyl with a biguanidide of the formula (III) or an acid addition salt thereof

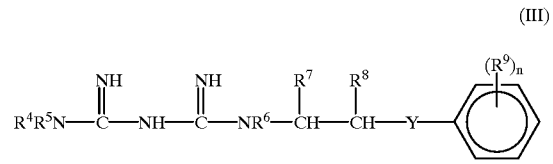

b) reacting a compound of the formula (IV),

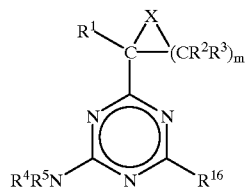

in which $R^{16}$ is an exchangeable radical or a leaving group, for example chlorine, trichloromethyl, ($C_1$–$C_4$) alkylsulfonyl and unsubstituted or substituted phenyl-($C_1$–$C_4$)alkylsulfonyl or ($C_1$–$C_4$)alkylphenylsulfonyl, with a suitable amine of the formula (V) or an acid addition salt thereof

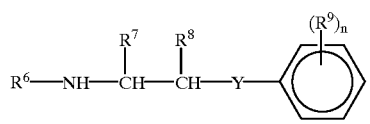

c) with reaction (nucleophilic substitution) of an exchangeable group on the triazine of the compound of the abovementioned formula (IV) or of the formula (X)

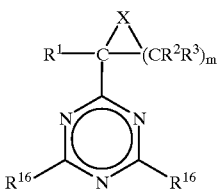

in which each of the radicals $R^{16}$ independently of one another is an exchangeable radical or a leaving group, for example chlorine, trichloromethyl, ($C_1$–$C_4$) alkylsulfonyl and unsubstituted or substituted phenyl-($C_1$–$C_4$)alkylsulfonyl, reacting this compound with a suitable aziridine of the formula (XI)

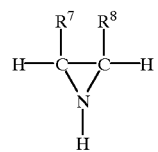

in which $R^7$ and $R^8$ are as defined for formula (I) and subsequently with a suitable nucleophile of the formula (XII)

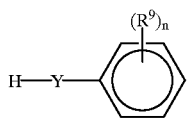

with ring opening of the aziridine ring, and, if a triazine of the formula (X) has been used, by reaction of the exchangeable group which is still present on the triazine framework with a compound of the formula $NHR^4R^5$ (ammonia or amine), or d) reacting a compound of the formula (XIII)

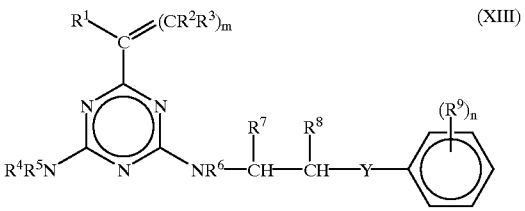

by epoxidization or cyclopropanization to give corresponding compounds of the formula (I), where, in the formulae (II), (III), (IV), (V), (X), (XI), (XII) and (XIII), the radicals $R^1$, $R^2$, $R^3$, $R^4$, $R^5$, $R^6$, $R^7$, $R^8$ and $R^9$ and also X, Y, m and n are as formula (I), with the proviso that in variant d) m is 1.

The reaction of the compounds of the formula (II) and (III) preferably takes place with base catalysis in an inert organic solvent, for example tetrahydrofuran (THF), dioxane, acetonitrile, dimethylformamide (DMF), methanol and ethanol, at temperatures between –10° C. and the boiling point of the solvent, preferably at from 20° C. to 60° C.; if acid addition salts of the formula (III) are used, these are generally liberated in situ with the aid of a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0] undec-7-ene (DBU). In this context the respective base is employed, for example, in the range from 0.1 to 3 mole equivalents relative to the compound of the formula (III). The compound of the formula (II) can, for example, be employed relative to the compound of the formula (III), in an equimolar quantity or with an excess of up to 2 mole equivalents. In principle, the appropriate methods are known in the literature (compare: Comprehensive Heterocyclic Chemistry, A. R. Katritzky, C. W. Rees, Pergamon Press, Oxford, N.Y., 1984, Vol.3; Part 2B; ISBN 0-08-030703-5, p.290).

The reaction of the compounds of the formula (IV) and (V) preferably takes place with base catalysis in an inert organic solvent, for example THF, dioxane, acetonitrile, DMF, methanol and ethanol, at temperatures between –10° C. and the boiling point of the respective solvent or solvent mixture, preferably at from 20° C. to 60° C., the compound (V), if employed as acid addition salt, being liberated if appropriate in situ with a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is generally employed in the range from 1 to 3 mole equivalents relative to the compound of the formula (IV), while the compound of the formula (IV) can, for example, be employed in equimolar quantities relative to the compound of the formula (V) or with an excess of up to 2 mole equivalents. In principle, the appropriate methods are known from the literature (Comprehensive Heterocyclic Chemistry, A. R. Katritzky, C. W. Rees, Pergamon Press, Oxford, N.Y., 1984, Vol.3; Part 2B; ISBN 0-08-030703-5, p. 482).

The precursors of the formulae (II), (III), (IV) and (V) are either commercially available or can be prepared by or in accordance with methods known from the literature. The compounds can also, for example, be prepared by one of the processes described below.

The compounds of the formula (III) can be prepared, for example, by reacting the amines of the formula (V) or salts thereof with cyanoguanidine in an inert solvent, such as, for example chlorobenzene or diethylene glycol or tetrahydrofuran or, if desired, water, in analogy to H. M. Eisa, A. S. Tantawy, M. M. El-Kerdawy, Pharmazie 46 (1991), 182–184. If appropriate, the addition of inorganic salts such as iron(III) chloride may accelerate the reaction or bring about a reduction in the reaction temperature (Sanwa Chem KK, JP 62215556).

The amines of the formula (V) or salts thereof can be prepared, for example, by reducing the corresponding oximes with, for example, LiAlH$_4$ (Bristol Labor. Inc. U.S. Pat. No. 2,703,324) or carrying out hydrogenation with hydrogen and Raney nickel (Suter, Zuter, Justus Liebigs Ann. Chem. 576 (1952), p. 215 ff., or else by reductive amination from the corresponding acetone derivatives (cf. A. Waefelaer et al. Bull. Soc. Chim. Belg. 85 (1976), 421–425).

The compound of the formula (IV), or a direct precursor thereof, can be prepared for example as follows:

1. By reaction of a compound of the formula (II) with an amidino-thiourea derivative of the formula (VI),

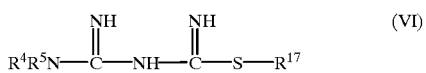

in which $R^{17}$ is $(C_1-C_4)$-alkyl or phenyl-$(C_1-C_4)$-alkyl and $R^4$ and $R^5$ are as defined for formula (I), giving compounds of the formula (IV) in which $R^{16}$ is —$SR^{17}$.

2. By reaction of a cyclic amidine of the formula (VII) or an acid addition salt thereof,

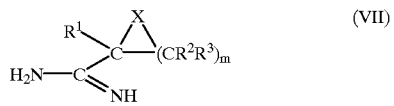

in which $R^1$, $R^2$, $R^3$, X and m are as defined for formula (I), with an N-cyanodithioiminocarbonate of the formula (VIII),

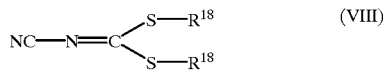

in which $R^{18}$ is $(C_1-C_4)$-alkyl or phenyl-$(C_1-C_4)$-alkyl, giving compounds of the formula (IV) in which $R^{16}$ is —$S$—$R^{18}$.

3. By reaction of an alkali metal dicyanamide with a cyclic carboxylic acid derivative of the abovementioned formula (II), giving compounds of the formula (IV) in which $R^{16}$ is $NH_2$.

4. By reaction of trichloroacetonitrile with a cyclic carbonitrile of the formula (IX)

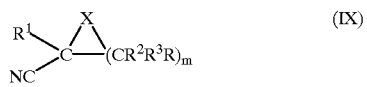

in which $R^1$, $R^2$, $R^3$, X and m are as defined for formula (I), giving first compounds of the formula (X), in which $R^{16}$ is $CCl_3$, which by subsequent reaction with compounds of the formula $HNR^4R^5$ ($R^4$ and $R^5$ as in formula (I)) lead to compounds of the formula (IV), in which $R^{16}$ is $CCl_3$.

If desired it is also possible, by analogy with the above processes under 1.-4., to prepare intermediates of the formula (X),

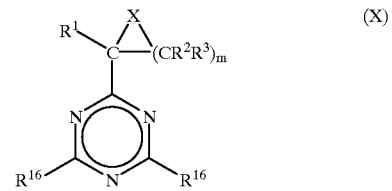

having 2 exchangeable groups $R^{16}$ (cf. formula (IV)) and to substitute the exchangeable groups in succession with appropriate amines or ammonia, in order, by analogy with generally known procedures, to obtain compounds of the formula (I).

If desired, it is possible to convert intermediates of the formula (X) obtained by analogy with the above processes under 1.-4., in which $R^{16}$ is $(C_1-C_4)$-alkylthio or phenyl-$(C_1-C_4)$-alkylthio, into more reactive derivatives of the formulae (X) by chlorination or oxidation.

It is likewise possible to prepare compounds of the formula (XIII) by methods known from the literature or by the abovementioned processes, in which case open-chain, olefinic derivatives are then employed by analogy with compounds of the formula (II), (VII), (IX) in which X was a C—C bond and m was 1.

The reaction of the carboxylic acid derivatives of the formula (II) with the amidinothiourea derivatives of the formula (VI) preferably takes place with base catalysis in an organic solvent, for example acetone, THF, dioxane, acetonitrile, DMF, methanol and ethanol, at temperatures from −10° C. to the boiling point of the solvent, preferably at from 0° C. to 20° C. However, the reaction can also be carried out in water or in aqueous solvent mixtures with one or more of the abovementioned organic solvents. If (VI) is employed as acid addition salt, it can if desired be liberated in situ with a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is employed in the range from 1 to 3 mole equivalents relative to the compound of the formula (VI). Compounds of the formula (II) and (VI) can, for example, be employed in equimolar quantities or with an excess of up to 2 mole equivalents of compound of the formula (II). In principle the appropriate methods are known from the literature (cf.: H. Eilingsfeld, H. Scheuermann, Chem. Ber.; 1967, 100, 1874); the corresponding intermediates of the formula (IV) are novel.

The reaction of the cyclic amidines of the formula (VII) with the N-cyanodithioiminocarbonates of the formula (VIII) preferably takes place with base catalysis in an inert organic solvent, for example acetonitrile, DMF, dimethylacetamide (DMA), N-methylpyrrolidone (NMP), methanol and ethanol, at temperatures from −10° C. to the boiling point of the solvent, preferably at from 20° C. to 80° C. If (VII) is employed as acid addition salt, it can if desired be liberated in situ with a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is employed in the range from 1 to 3 molar equivalents relative to the compound of the formula (VIII); compounds of the formula (VII) and (VII) can in general be employed in equimolar quantities or with an excess of 2 mole equivalents of compound of the formula (II). In principle the appropriate methods are known from the literature (cf.: T. A. Riley, W. J. Henney, N. K. Dalley, B. E. Wilson, R. K. Robins; J. Heterocyclic Chem.; 1986, 23 (6), 1706–1714); the corresponding intermediates of the formula (IV) are novel.

Intermediates of the formula (X) where $R^{16}$=chlorine can be prepared by reacting alkali metal dicyanamide with a cyclic carboxylic acid derivative of the formula (II), in which case $R^{15}$ is preferably the functional group carbonyl chloride or carboxamide. The reaction components are, for example, reacted with acid catalysis in an inert organic solvent such as toluene, chlorobenzene, or chlorinated hydrocarbons at temperatures between −10° C. and the boiling point of the solvent, preferably at from 20° C. to 80° C., it being possible to chlorinate the resulting intermediates in situ using an appropriate chlorinating reagent, for example phosphorus oxychloride. Examples of suitable acids are hydrohalic acids such as HCl or else Lewis acids, for example $AlCl_3$ or $BF_3$ (cf. U.S. Pat. No. 5,095,113, DuPont).

Intermediates of the formula (X) where $R^{16}$=trihalomethyl can be prepared by reacting the corresponding trihaloacetonitriles with a cyclic carbonitrile of the formula (IX). The reaction components are, for example, reacted with acid catalysis in an inert organic solvent such as toluene, chlorobenzene or chlorinated hydrocarbons at temperatures between −40° C. and the boiling point of the solvent, preferably at from −10° C. to 30° C. Examples of suitable acids are hydrohalic acids such as HCl or else Lewis acids such as $AlCl_3$ or $BF_3$ (cf. EP-A-130939, Ciba Geigy).

Intermediates of the formula (IV) or (X), in which $R^{16}$ is ($C_1$–$C_4$)alkylmercapto or unsubstituted phenyl-($C_1$–$C_4$)-alkylmercapto, can be converted in an inert organic solvent, for example toluene, chlorobenzene, chlorinated hydrocarbons or others, at temperatures between −40° C. and the boiling point of the solvent, preferably at from 20° C. to 80° C., using an appropriate chlorinating reagent, for example elemental chlorine or phosphorus oxychloride, to more reactive chlorotriazines of the formula (IV) or (X), in which $R^{16}$ is Cl (cf. J. K. Chakrabarti, D. E. Tupper; Tetrahedron 1975, 31(16), 1879–1882).

Intermediates of the formula (IV) or (X), in which $R^{16}$ is ($C_1$–$C_4$)alkylmercapto or unsubstituted or substituted phenyl-($C_1$–$C_4$)-alkylmercapto or ($C_1$–$C_4$)alkylphenylthio can be oxidized in appropriate solvent, for example chlorinated hydrocarbons, acetic acid, water, alcohols, acetone or mixtures thereof, at temperatures between 0° C. and the boiling point of the solvent, preferably from 20° C. to 80° C., using a suitable oxidation reagent such as m-chloroperbenzoic acid, hydrogen peroxide, potassium peroxomonosulfate (cf.: T. A. Riley, W. J. Henney, N. K. Dalley, B. E. Wilson, R. K. Robins; J. Heterocyclic Chem.; 1986, 23 (6), 1706–1714).

Compounds analogous to the formula (IV) are also obtained by selective nucleophilic substitution of an exchangeable group in compounds analogous to the formula (X), in which $R^{16}$ is, for example, halogen, perhalomethyl, ($C_1$–$C_4$)alkylsulfinyl, ($C_1$–$C_4$)alkylsulfonyl or other leaving groups known from the literature, in an appropriate solvent such as THF, dioxane, alcohols, DMF or acetonitrile or mixtures thereof, at temperatures between −10° C. and the boiling point of the solvent, preferably at from 10° C. to 25° C., under basic conditions if desired. Suitable bases are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is employed in the range from 1 to 3 mole equivalents relative to the compound of formula (X); the nucleophile is in general employed in equimolar quantities in an excess of up to 2 mole equivalents and can also if desired be used itself as base. In principle, the appropriate methods known from the literature (cf.: V. I. Kaelarev, Dibi Ammar, A. F. Lunin; Ximinya Geterosikl. Soedin., 1985, N11, 1557–1563).

In an analogous manner it is possible, by substitution of a leaving group of triazines of the formula (IV) or (X) with aziridines of the formula (XI), with or without the addition of a base in a suitable inert solvent such as THF, dioxane, alcohols, DMF or acetonitrile or mixtures thereof, at temperatures between −10 ° C. and the boiling point of the solvent, preferably at from 20° C. to 80° C., to prepare aziridinyl triazines. Suitable bases are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is employed in the range of from 1 to 3 mole equivalents relative to the compound of formula (IV) or (X); the aziridine can be employed in an excess of up to 3 mole equivalents and can also if desired be used itself as base. Subsequently, the aziridine ring can be opened. For this purpose the intermediate compounds are reacted, for example in an appropriate solvent such as THF, dioxane, alcohols, DMF or acetonitrile, with nucleophiles of the formula (XII) at temperatures between −10° C. and the boiling point of the solvent, preferably at from 20° C. to 80° C. The method of ring opening is known in principle (cf.: M. D. Nair, J. D. Nagarajan, Indian J. Chem.; 1985, 24B, 940; or JP 03005466; Chem. Abstracts 115:4914); the ring opening in triazinyl derivatives is novel.

For the preparation of the acid addition salts of the compounds of the formula (I), suitable acids are the following: hydrohalic acids such as hydrochloric acid or hydrobromic acid, and also phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition compounds of the formula (I) can be obtained in a simple manner by the customary methods of forming salts, for example by dissolving a compound of the formula (I) in an appropriate organic solvent such as, for example, methanol, acetone, methylene chloride or benzine and adding the acid at temperatures from 0 to 100° C., and can be isolated in a known manner, for example by filtration, and can if desired be purified by washing with an inert organic solvent.

The base addition salts of the compounds of formula (I) are preferably prepared in inert polar solvents such as, for example, water, methanol or acetone at temperatures from 0 to 100° C. Examples of suitable bases for preparing the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alcoholates and alkaline earth metal alcoholates, for example sodium methanolate and potassium tert-butylate, or ammonia or ethanolamine.

By the "inert solvents" mentioned in the above process variants, solvents are meant which are in each case inert under the respective reaction conditions but which need not be inert under any reaction conditions.

The novel compounds of the formula (I) and the salts thereof, referred to together below as (novel) compounds of the formula (I), have an outstanding herbicidal activity against a broad spectrum of economically important monocotyledon and dicotyledon weeds. The active compounds also act effectively against difficult-to-control perennial weeds which produce shoots from rhizomes, rootstocks or other perennial organs. In this context it does not matter whether the substances are applied before sowing, pre-emergence or post-emergence.

Individually, examples may be mentioned of some representatives of the monocotyledon and dicotyledon weed flora which can be controlled by the compounds according to the invention, without such mention being intended to restrict the invention to specific species.

Examples of monocotyledon weed species against which the active compounds act effectively are Avena, Lolium, Alopecurus, Phalaris, Echinochloa, Digitaria, Setaria and Cyperus species from the annual group and, among the perennial species, Agropyron, Cynodon, Imperata and Sorghum and also perennial Cyperus species.

In the case of dicotyledon weed species, the spectrum of action extends to species such as, for example, Galium, Viola, Veronica, Lamium, Stellaria, Amaranthus, Sinapis, Ipomoea, Matricaria, Abutilon and Sida among the annuals and Convolvulus, Cirsium, Rumex and Artemisia among the perennial weeds.

The novel active compounds also display outstanding control of weeds which occur under the specific growing conditions in rice, examples being Sagittaria, Alisma, Eleocharis, Scirpus and Cyperus.

Where the novel compounds are applied to the surface of the soil before germination, either the weed seedlings are prevented completely from emerging, or the weeds grow until they reach the cotyledon stage, but then stop growing and, finally, die off completely after three to four weeks have elapsed.

Where the active compounds are applied post-emergence to the green parts of plants, there is likewise a very rapid and drastic termination of growth after treatment, and the weed plants remain at the growth stage they were at at the time of application, or die off completely after a certain time, so that in this manner competition from weeds, which is damaging to the crop plants, is eliminated very early on and in a sustained manner.

Even though the novel compounds have an excellent herbicidal activity with respect to monocotyledon and dicotyledon weeds, crop plants of economically important crops, for example wheat, barley, rye, rice, maize, sugar beet, cotton and soya, suffer only minimal or zero damage. For these reasons the present compounds are highly suitable for the selective control of unwanted plant growth in crops of agriculturally useful plants.

Furthermore, the substances according to the invention exhibit outstanding growth-regulating properties in crop plants. They intervene with a regulatory action in the endogenous plant metabolism and can therefore be employed for the targeted control of plant contents and for facilitating the harvest, for example by provoking desiccation and stunted growth. Moreover, they are also suitable for generally controlling and inhibiting unwanted vegetative growth without killing the plants in doing so. In the case of numerous monocotyledon and dicotyledon crops, inhibition of vegetative growth plays an important role, since it allows lodging to be reduced or prevented completely.

The novel compounds can be applied in the customary formulations in the form of wettable powders, emulsifiable concentrates, sprayable solutions, dusts or granules. The invention therefore also provides herbicidal and plant growth-regulating compositions comprising compounds of the formula (I).

The compounds of the formula (I) can be formulated in various ways depending on the prevailing biological and/or chemico-physical parameters. Examples of suitable formulation options are wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, micro-capsules and waxes.

These individual formulation types are known in principle and are described for example in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, New York, 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described for example in Watkins, "Handbook of Insecticide Dust Diluents and Carriers", 2nd Ed., Darland Books, Caldwell N. J., H. V. Olphen, "Introduction to Clay Colloid Chemistry"; 2nd Ed., J. Wiley & Sons, New York; C. Marsden, "Solvents Guide"; 2nd Ed., Interscience, New York 1963; McCutcheon's "Detergents and Emulsifiers Annual", M. C. Publ. Corp., Ridgewood N.J.; Sisley and Wood, "Encyclopedia of Surface Active Agents", Chem. Publ. Co. Inc., New York 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, for example insecticides, acaricides, herbicides and fungicides, and also with safeners, fertilizers and/or growth regulators, for example in the form of a readymix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate. To prepare the wettable powders, the herbicidal active compounds are finely ground, for example in customary apparatus such as hammer mills, fan mills and air jet mills, and are mixed simultaneously or subsequently of the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material. For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8–57.

For further details on the formulation of crop protection products, see for example G. C. Klingman, "Weed Control as a Science", John Wiley and Sons Inc., New York, 1961, pages 81–96 and J. D. Freyer, S. A. Evans, "Weed Control Handbook", 5th Ed., Blackwell Scientific Publications, Oxford, 1968, pages 101–103.

The agrochemical formulations generally contain from 0.1 to 99% by weight, in particular from 0.1 to 95% by weight, of active compound of the formula (I). In wettable powders the concentration of active compound is for example from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably and commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination (co-components) for the novel active compounds in mixed formulations or in a tank mix are, for example, known active compounds, as described for example in Weed Research 26, 441–445 (1986), or "The Pesticide Manual", 10th edition, The British Crop Protection Council and the Royal Soc. of Chemistry, 1994, England, and literature cited therein. Examples of herbicides which are known from the literature and can be combined with the compounds of the formula (I) are the following active compounds (Note: The compounds are denoted either by their "common name" in accordance with the International Organization for Standardization (ISO) or by their chemical name, together if appropriate with a customary code number):

acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; azimsulfurone (DPX-A8947); aziprotryn; barban; BAS 516 H, i.e. 5-fluor-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethylthiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (e.g. clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (e.g. butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin;

dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (e.g. ethyl ester, HN-252); etobenzanid (HW 52); fenoprop; fenoxan, fenoxaprop and fenoxaprop-P and esters thereof, for example fenoxaprop-P-ethyl and fenoxaprop-ethyl; fenoxydim; fenuron; flampropmethyl; flazasulfuron; fluazifop and fluazifop-P and esters thereof, for example fluazifop-butyl and fluazifop-P-butyl; fluchloralin; flumetsulam; flumeturon; flumiclorac and its esters (e.g. pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (e.g. methyl ester, NC-319); haloxyfop and its esters; haloxyfop-P (=R-haloxyfop) and its esters; hexazinone; imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuronmethyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenopbutyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (e.g. propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuronmethyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thizopyr (Mon-13200); thidiazimin (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations in customary commercial form are, if desired, diluted in a customary manner, for example using water in the case of wettable powders, emulsifiable concentrates, dispersions and water-dispersible granules. Preparations in the form of dusts, granules for soil application or broadcasting, and also sprayable solutions are not normally diluted further with additional inert substances prior to use.

The required application rate of the compounds of the formula (I) varies with the external conditions, such as temperature, humidity, nature of the herbicide used, etc. It can vary within broad limits, for example between 0.001 and 10.0 kg/ha or more of active substance, but is preferably between 0.005 and 5 kg/ha.

A. CHEMICAL EXAMPLES

Example 1

2-Amino-4-(2-methyl-1-oxaspiro[2.4]heptan-2-yl)-6-(1-(3,5-dimethylphenoxy)-propyl-2-amino)-1,3,5-triazine a) 9.3 g (0.11 mol) of cyclopentanone and 13.5 g (0.11 mol) of methyl 2-chloropropionate are cooled to 0 to 2° C.; at this temperature, 13.6 g (0.12 mol) of potassium tert-butylate suspended in 200 ml of tetrahydrofuran are added slowly dropwise with stirring over a period of about 90 minutes, after which the mixture is stirred for a further 60 minutes without cooling. A little water is added to the reaction mixture, which is subjected to extraction with diethyl ether; the organic phase is dried over sodium sulfate, the drying agent is filtered off, and evaporation of the solvent gives 10.6 g of methyl 2-methyl-1-oxaspiro[2.4]heptane-2-carboxylate, which can be employed without further purification in the subsequent stage (see b).

b) A methanolate solution prepared from 0.86 g (0.036 mol) of sodium and 50 ml of methanol is added to 5.4 g (0.018 mol) of 2-biguanidino-1-(3,5-dimethylphenoxy) propane hydrochloride in 50 ml of methanol and 6 g of ground 3A molecular sieve. 5.3 g (0.028 mol) of methyl 2-methyl-1-oxaspiro-[2.4]heptane-2-carboxylate are then added and the mixture is stirred for 2 hours at 25° C. and then for 4 hours at 65° C. The reaction mixture is filtered, the filtrate is concentrated and the residue is taken up in ethyl acetate. This solution is washed with water, and the organic phase is separated off and dried over sodium sulfate. The drying agent is filtered off and the ethyl acetate phase is concentrated by evaporation. Separation by column chromatography over silica gel using ethyl acetate as eluent gives 1.8 g (25% of theory) of 2-amino-4-(2-methyl-1-oxaspiro[2.4]heptan-2-yl)-6-(1-(3,5-dimethylphenoxy)-propyl-2-amino)-1,3,5-triazine.

Example 19
2-Amino-4-cyclobutyl-6-(1-(3,5-dimethylphenoxy)-propyl-2-amino)-1,3,5-triazine A methanolate solution prepared from 1.2 g (0.05 mol) of sodium and 100 ml of methanol is added to 7.2 g (0.025 mol) of 2-biguanidino-1-(3,5-dimethylphenoxy)-propane hydrochloride in 50 ml of methanol and 7 g of ground 3A molecular sieve. 5.2 g (0.045 mol) of ethyl cyclobutane carboxylate are then added and the mixture is stirred for 2 hours at 25° C. and then for 4 hours at 65° C. The reaction mixture is filtered, the filtrate is concentrated and the residue is taken up in ethyl acetate. This solution is washed with water, and the organic phase is separated off and dried over sodium sulfate. The drying agent is filtered off and the ethyl acetate phase is concentrated by evaporation. Separation by column chromatography over silica gel using ethyl acetate as eluent gives 3.5 g (39% of theory) of 2-amino-4-cyclobutyl-6-(1-(3,5-dimethylphenoxy)-propyl-2-amino)-1,3,5-triazine.

Example 29
2-Amino-4-cyclopropyl-6-(1-(4-chloro-3,5-dimethylphenoxy)-propyl-2-amino)-1,3,5-triazine A ethanolate solution prepared from 1.5 g (0.06 mol) of sodium and 100 ml of ethanol is added to 10.3 g (0.03 mol) of 2-biguanidino-1-(4-chloro-3,5-dimethylphenoxy)-propane hydrochloride in 50 ml of ethanol and 10 g of ground 3A molecular sieve. 5.2 g (0.045 mol) of ethyl cyclopropane carboxylate are then added and the mixture is stirred for 2 hours at 25° C. and then for 4 hours at 65° C. The reaction mixture is filtered, the filtrate is concentrated and the residue is taken up in ethyl acetate. This solution is washed with water, and the organic phase is separated off and dried over sodium sulfate. The drying agent is filtered off and the ethyl acetate phase is concentrated by evaporation. Separation by column chromatography over silica gel using ethyl acetate as eluent gives 1.5 g (14% of theory) of 2-amino-4-cyclopropyl-6-(1-(4-chloro-3,5-dimethylphenoxy)-propyl-2-amino)-1,3,5-triazine.

The compounds described in Table 1 are obtained in analogy to the above examples 1, 19 and 29. In the table:

No.=Example or Example number m.p.=Melting point (fusion point) in °C. or an indication on the aggregate state or another indication, for example I, II=diastereomer (mixture) I or II Me=methyl Et=ethyl Pr=propyl i-Pr=isopropyl c-Pr=cyclopropyl t-Bu=tertiary-butyl Ph=phenyl Figures=1. Figure before substituents denotes position of the substituent on the aromatic structure 2. Figure before heterocyclic radicals denotes position of radical relative to heteroatom, for example 2-Pyridyl=-2-pyridine=pyrid-2-yl Cyclobutylene=cyclobut-1,1-diyl

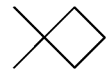

Cyclopentylene=cyclopent-1,1-diyl

Cyclohexylene=cyclohex-1,1-diyl

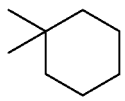

Morpholino=-morpholine=

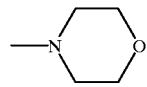

Piperidino=-piperidine=

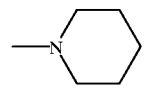

2-Thienyl=-2-thieno=

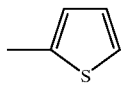

TABLE 1

Compounds of the formula (I)

$$\begin{array}{c} R^1 \\ \diagdown \\ C \\ \diagup \quad \diagdown \\ X \quad (CR^2R^3)_m \end{array} \text{— pyrimidine —} NR^6-CHR^7-CHR^8-Y-\text{Ph}(R^9)_n \quad (1)$$

| No | $R^1$ | $(CR^2R^3)_m$ | $R^4$ | $R^5$ | $R^6$ | $R^7$ | $R^8$ | $(R^9)_n$ | X | Y | M.p. |
|---|---|---|---|---|---|---|---|---|---|---|---|
| 1 | Me | Cyclopentylene | H | H | H | Me | H | 3,5-$Me_2$ | O | O | 80–81 |
| 2 | Me | Cyclohexylene | H | H | H | Me | H | 3,5-$Me_2$ | O | O |  |
| 3 | H | CHCH=$CMe_2$ | H | H | H | Me | H | 3,5-$Me_2$ | $CMe_2$ | O | 110–111 |
| 4 | H | CHCH=$CMe_2$ | H | H | H | H | H | 2,4-$Me_2$ | $CMe_2$ | O | liquid |
| 5 | H | CHCH=$CMe_2$ | H | H | H | H | H | 3,4-$(MeO)_2$ | $CMe_2$ | — | liquid |
| 6 | Me | $CCl_2$ | H | H | H | Me | H | 3,5-$Me_2$ | $CH_2$ | O | liquid |
| 7 | Me | $CCl_2$ | H | H | H | Me | H | 4-Cl | $CH_2$ | O | 58–62 |
| 8 | Cl | $CEt_2$ | H | H | H | Me | Me | 3,5-$Me_2$ | O | O |  |
| 9 | Cl | CHEt | H | H | H | Me | Me | 3,5-$Me_2$ | O | O |  |
| 10 | Cl | CHEt | H | H | H | H | H | 3,5-$Me_2$ | O | O |  |
| 11 | Cl | CHEt | H | H | H | Me | H | 3,5-$Me_2$ | O | O |  |
| 12 | H | $CF_2$ | H | H | H | Me | H | 3,5-$Me_2$ | $CH_2$ | O | solid 52–55 |
| 13 | Me | $CH_2$ | H | H | H | Me | H | 3,5-$Me_2$ | O | O |  |
| 14 | Me | $CH_2$ | H | H | H | H | H | 3-Me, 4,5-O$CH_2$O— | $CH_2$ | O |  |
| 15 | F | $CH_2$ | H | H | H | Me | Me | 3,5-$Me_2$ | $CH_2$ | O |  |
| 16 | Et | $CH_2$ | H | H | $CH_2$OMe | Me | H | 3,5-$Me_2$ | O | O | liquid |
| 17 | H | $CH_2$ | H | H | H | H | H | 3-Me, 4,5-O$CH_2$O— | $CH_2$ | O |  |
| 18 | F | $CH_2$ | H | H | H | Me | H | 3,5-$Me_2$ | $CH_2$ | O |  |
| 19 | H | $CH_2CH_2$ | H | H | H | H | H | 4,5-$Me_2$ | $CH_2$ | O |  |
| 20 | Me | $CH_2$ | H | H | H | Me | H | 3,5-$Me_2$ | N-Me | O |  |
| 21 | Me | $CH_2$ | H | H | H | Me | —$(CH_2)_4$— |  | $CH_2$ | O |  |
| 22 | Me | $CH_2$ | H | H | H | Me | H | 3,5-$(i$-Bu$)_2$ | $CH_2$ | O | solid |
| 23 | Me | $CH_2$ | H | H | H | Me | H | 3,5-$Me_2$ | O | O |  |
| 24 | F | $CH_2$ | H | H | H | Me | H | 3,5-$Me_2$ | $CH_2$ | O |  |
| 25 | Me | $CH_2$ | H | H | H | Me | H | 4-Cl | O | O | solid |
| 26 | Me | $CH_2$ | H | H | H | Me | H | 3,5-$Me_2$ | $CH_2$ | NH |  |
| 27 | H | $CH_2$ | H | H | H | Me | H | 3,5-$Me_2$ | $CH_2$ | O |  |
| 28 | Me | $CH_2$ | H | H | H | Me | H | 3,5-$Me_2$ | O | S |  |

TABLE 1-continued

Compounds of the formula (I)

$$R^4R^5N \text{-pyrimidine-} NR^6\text{—}CHR^7\text{—}CHR^8\text{—}Y\text{—}(C_6H_{4-n}(R^9)_n)$$
with $R^1\text{—}C(X)(CR^2R^3)_m$ substituent (1)

| No | $R^1$ | $(CR^2R^3)_m$ | $R^4$ | $R^5$ | $R^6$ | $R^7$ | $R^8$ | $(R^9)_n$ | X | Y | M.p. |
|---|---|---|---|---|---|---|---|---|---|---|---|
| 29 | H | $CH_2$ | H | H | H | Me | H | 3,5-$Me_2$ | $CH_2$ | O | 143–144 |
| 30 | n-Pr | $CH_2$ | H | H | H | H | H | 4-Cl | $CH_2$ | O | |
| 31 | Me | $CH_2$ | H | H | H | Me | H | 3,5-$Me_2$ | $CH_2$ | O | 63–65 |
| 32 | Ph | $CH_2$ | H | H | H | Me | H | 3,5-$Me_2$ | $CH_2$ | O | |
| 33 | OMe | $CH_2$ | H | H | H | Me | H | 4-Cl | $CH_2$ | O | |
| 34 | Me | $CH_2$ | H | H | H | Et | H | 3,5-$Me_2$ | $CH_2$ | O | |
| 35 | Me | $CH_2$ | H | H | Me | H | H | 3,5-$Me_2$ | O | O | |
| 36 | Me | $CH_2$ | H | H | H | Me | H | 3,5-$Me_2$ | $CH_2$ | NMe | |
| 37 | Me | $CH_2$ | H | H | H | Me | H | 3,4,5-$Me_3$ | $CH_2$ | O | 115–116 |
| 38 | Me | $CH_2CH_2CH_2$ | CHO | H | H | Et | H | 3,5-$Me_2$ | $CH_2$ | O | liquid |
| 39 | H | $CH_2$ | H | H | H | Me | H | 3,5-$Me_2$ | $CH_2$ | O | liquid |
| 40 | F | $CH_2$ | H | H | H | Me | H | 3,5-$Me_2$ | N-Me | O | |
| 41 | Me | $CH_2$ | H | H | H | i-Pr | H | 3,5-$Me_2$ | $CH_2$ | O | |
| 42 | Me | $CH_2$ | H | H | H | H | H | 3-Me, 4,5-$OCH_2O$— | O | O | |
| 43 | H | $CH_2$ | H | H | H | Me | H | 3,5-$Me_2$ | O | O | |
| 44 | Me | $CH_2$ | H | H | CHO | Me | H | 3,5-$Me_2$ | $CH_2$ | O | 87–90 |
| 45 | F | $CH_2$ | H | COMe | H | Me | H | 4-t-Bu | $CH_2$ | O | |
| 46 | Me | $CH_2$ | H | H | H | Me | H | 4-t-Bu | $CH_2$ | O | 104–106 |
| 47 | Me | $CH_2CH_2$ | H | H | H | Me | H | 4-t-Bu | $CH_2$ | O | |
| 48 | Me | $CH_2$ | H | H | H | Me | H | 3,5-$Me_2$ | $CH_2$ | S | |
| 49 | Me | $CH_2$ | H | H | H | Me | —$(CH_2)_4$— | 3,4,5-$Me_3$ | $CH_2$ | O | |
| 50 | Me | $CH_2$ | H | Me | H | H | H | 3,5-$Me_2$ | $CH_2$ | O | |
| 51 | Me | $CH_2$ | Me | H | H | Me | H | 3,4,5-$Me_3$ | $CH_2$ | O | |
| 52 | OMe | $CH_2$ | H | H | H | Me | H | 3,5-$Me_2$ | $CH_2$ | O | |
| 53 | OMe | $CH_2CH_2CH_2$ | H | CHO | H | Me | H | 3,5-$Me_2$ | $CH_2$ | O | |
| 54 | F | $CH_2$ | Me | Me | Me | H | H | 3,5-$Me_2$ | $CH_2$ | O | |
| 55 | Me | $CH_2$ | H | Et | Me | H | H | 2,3-$Me_2$ | $CH_2$ | O | |
| 56 | Me | $CH_2$ | Et | Et | H | H | H | 3,5-$Me_2$ | $CH_2$ | O | |
| 57 | Me | $CH_2$ | H | H | H | H | H | 3,5-$Me_2$ | $CH_2$ | O | |
| 58 | Me | $CH_2$ | H | H | H | H | H | 3,5-$Me_2$ | $CH_2$ | O | |
| 59 | F | $CH_2$ | H | H | H | Me | H | 3,4,5-$Me_3$ | $CH_2$ | S | |
| 60 | Me | $CH_2$ | H | H | H | Me | H | 3,4,5-$Me_3$ | $CH_2$ | O | |
| 61 | i-Pr | $CH_2$ | H | H | H | H | H | 3,5-$Me_2$ | $CH_2$ | O | |

TABLE 1-continued

Compounds of the formula (I)

| No | R¹ | (CR²R³)ₘ | R⁴ | R⁵ | R⁶ | R⁷ | R⁸ | (R⁹)ₙ | X | Y | M.p. |
|---|---|---|---|---|---|---|---|---|---|---|---|
| 62 | F | CH₂ | H | H | H | Me | H | 3,5-Me₂ | CH₂ | CH₂ | solid |
| 63 | H | CH₂CH₂ | H | H | H | Et | H | 3,5-Me₂ | N-Me | O | |
| 64 | Br | CH₂ | H | H | H | Me | H | 3,5-Me₂ | CH₂ | O | |
| 65 | F | CH₂ | H | H | H | Me | H | 4-Cl | CH₂ | O | 124–126 |
| 66 | Me | CH₂ | H | H | CH₂OMe | Me | H | 3,5-Me₂ | CH₂ | O | |
| 67 | Me | CH₂ | H | H | H | H | H | 3,5-Me₂ | CH₂ | CH₂ | |
| 68 | H | CH₂ | H | H | CH₂OMe | Me | H | 2,4-Me₂ | CH₂ | O | |
| 69 | Me | CH₂ | H | H | H | H | H | 3,5-Me₂ | CH₂ | O | liquid |
| 70 | Et | CH₂ | H | Me | H | Me | H | 3,5-Me₂ | CH₂ | O | liquid |
| 71 | Me | CH₂ | Me | H | CHO | H | H | 2,3,5-Me₃ | CH₂ | O | |
| 72 | Me | CH₂ | H | H | H | Me | H | 3,5-Me₂ | CH₂ | S | |
| 73 | H | CH₂ | H | H | H | H | H | 3,5-Me₂ | CH₂ | O | solid |
| 74 | Me | CH₂ | H | H | H | Me | H | 3,4-Me₂ | CH₂ | O | liquid |
| 75 | Me | CH₂ | H | H | H | H | H | 3,5-Me₂ | N-Me | O | liquid |
| 76 | Me | CH₂ | H | H | H | Me | H | 4-OCH₃ | CH₂ | O | 58–60 |
| 77 | Me | CH₂ | H | H | H | Me | H | 2,3-Me₂ | CH₂ | O | |
| 78 | Me | CH₂ | H | H | H | Me | Me | 2,3-Me₂ | CH₂ | O | |
| 79 | OMe | CH₂ | H | H | H | H | H | 2,3-Me₂ | O | O | |
| 80 | Me | CH₂CH₂ | H | H | H | Me | H | 3,5-Me₂ | CH₂ | O | |
| 81 | OMe | CH₂ | H | H | H | Me | Me | 3,4-(MeO)₂ | CH₂ | O | |
| 82 | H | CH(i-Pr) | H | H | H | H | H | 3,5-Me₂ | O | — | |
| 83 | Cl | CMeCF₃ | H | H | H | Me | H | 3,5-Me₂ | CH₂ | O | |
| 84 | H | CHMe | H | H | H | Me | H | 3,5-Me₂ | O | O | |
| 85 | Me | CHMe | H | H | H | Me | H | 3,5-Me₂ | O | S | |
| 86 | H | CHMe | H | H | H | Me | H | 4-Cl | CH₂ | O | 58–60 |
| 87 | Me | CHMe | H | H | H | Me | H | 3,5-Me₂ | CH₂ | O | liquid |
| 88 | H | CHMe | H | H | H | Me | H | 3,5-Me₂ | CH₂ | CH₂ | |
| 89 | F | CHMe | H | H | Et | Me | H | 3,5-Me₂ | O | O | |
| 90 | Me | CHMe | Me | Me | H | Me | H | 3,5-Me₂ | CH₂ | O | |
| 91 | Me | CMe₂ | Me | Me | Me | H | Me | 2,6-Me₂ | CH₂ | O | |
| 92 | H | CMe₂ | H | H | H | Me | H | 3,5-Cl₂ | O | O | |
| 93 | Me | CMe₂ | H | H | H | Me | H | 3,5-Me₂ | O | O | solid |
| 94 | Me | CMe₂ | H | H | H | Me | H | 3,5-Me₂ | O | O | |

TABLE 1-continued

Compounds of the formula (I)

$$R^4R^5N \text{ -- pyrimidine -- } NR^6\text{--}CHR^7\text{--}CHR^8\text{--}Y\text{--}C_6H_{(5-n)}(R^9)_n \quad (1)$$

with $R^1, X, C, (CR^2R^3)_m$ substituents on the pyrimidine

| No | $R^1$ | $(CR^2R^3)_m$ | $R^4$ | $R^5$ | $R^6$ | $R^7$ | $R^8$ | $(R^9)_n$ | X | Y | M.p. |
|---|---|---|---|---|---|---|---|---|---|---|---|
| 95 | Me | CMe$_2$ | H | H | H | Me | H | 3,5-Me$_2$ | O | S | solid |
| 96 | H | CMe$_2$ | H | H | H | Me | H | 3,5-Me$_2$ | CMe$_2$ | O | |
| 97 | Me | CMe$_2$ | H | H | Me | Me | Me | 3,5-Me$_2$ | O | O | |
| 98 | Me | CMe$_2$ | H | H | Me | Me | H | 3,5-Me$_2$ | O | O | |
| 99 | Me | CMe$_2$ | H | H | Me | Me | H | 4-t-Bu | O | O | |
| 100 | Me | CMe$_2$ | H | H | Me | Me | H | 3,4,5-Me$_3$ | O | O | |
| 101 | H | CMe$_2$ | H | H | H | Me | H | 3,5-Me$_2$ | O | O | 168–170 |
| 102 | H | CMePh | H | H | H | H | H | 2,4-Me$_2$ | O | O | 119–120 |
| 103 | H | CMePh | H | H | H | Me | H | 3,5-Me$_2$ | O | O | I: 153–155 |
| 104 | H | CMePh | H | H | H | Me | H | 3,5-Me$_2$ | O | O | II: 125–128 |
| 105 | F | CHPh | H | H | H | Me | H | 3,5-Me$_2$ | CH$_2$ | O | 77–78 |
| 106 | Me | Cyclopentylene | H | H | H | Me | H | 4-Cl | O | O | |
| 107 | Me | CHMe | H | H | H | Me | H | 3,5-Me$_2$ | O | O | liquid |
| | | | | | | | | 4-Cl | | | |
| 108 | Me | CMe$_2$ | H | H | H | Me | H | 3,5-Me$_2$ | O | O | 88–90 |
| | | | | | | | | 4-Cl | | | |
| 109 | Me | CMe$_2$ | H | H | H | Me | H | 3,5-Me$_2$ | O | O | 89–90 |
| 110 | Me | CHMe | H | H | H | Me | H | 3,5-Me$_2$ | O | O | 64–65 |
| 111 | Me | Cyclopentylene | H | H | H | Me | H | 4-Cl | O | O | |
| 112 | Cl | CMe$_2$ | H | H | H | H | H | 2,4-Me$_2$ | O | O | |
| 113 | Cl | CMe$_2$ | H | H | H | Me | H | 3,5-Me$_2$ | O | O | |
| | | | | | | | | 4-Cl | | | |
| 114 | Cl | CMe$_2$ | H | H | H | Me | H | 3,5-Me$_2$ | O | O | |
| 115 | Cl | Cyclopentylene | H | H | H | Me | H | 3,5-Me$_2$ | O | O | |
| 116 | F | Cyclopentylene | H | H | H | Me | H | 3,5-Me$_2$ | O | O | |
| 117 | F | CMe$_2$ | H | H | H | Me | H | 3,5-Me$_2$ | O | O | |
| | | | | | | | | 4-Cl | | | |
| 118 | F | CMe$_2$ | H | H | H | Me | H | 3,4,5-Me$_3$ | O | O | |
| 119 | F | CMe$_2$ | H | H | H | Me | H | 3,5-Me$_2$ | O | O | |
| 120 | F | Cyclopentylene | H | H | H | Me | H | 3,5-Me$_2$ | O | O | |
| 121 | Me | CH$_2$ | H | H | H | Me | Me | 3,5-Me$_2$ | CH$_2$ | O | |
| 122 | Me | CH$_2$ | H | H | H | Me | Me | 3,5-Me$_2$ | O | O | |
| 123 | Me | CMe$_2$ | H | H | H | Me | Me | 3,5-Me$_2$ | O | O | |

TABLE 1-continued

Compounds of the formula (I)

$$R^4R^5N \text{-pyrimidine-} NR^6-CH(R^7)-CH(R^8)-Y-\text{Ph}(R^9)_n, \text{ with } R^1-C(X)-(CR^2R^3)_m \text{ substituent} \quad (1)$$

| No | $R^1$ | $(CR^2R^3)_m$ | $R^4$ | $R^5$ | $R^6$ | $R^7$ | $R^8$ | $(R^9)_n$ | X | Y | M.p. |
|---|---|---|---|---|---|---|---|---|---|---|---|
| 124 | Me | CMe$_2$ | H | H | H | Me | Me | 3,5-Me$_2$ | O | O | |
| 125 | Me | Cyclopentylene | H | H | H | Me | Me | 3,5-Me$_2$ | O | O | |
| 126 | C≡CMe | CH$_2$ | H | H | NH$_2$ | Me | H | 2,3-(CH$_2$)$_5$ | CH$_2$ | O | |
| 127 | SCN | CH$_2$ | Me | H | CH$_2$C≡CH | Et | H | 2,3-(CH$_3$)$_4$ | O | O | |
| 128 | CN | CH$_2$—CH$_2$ | Me | Me | CH$_2$CN | Pr | H | 2,3-(CH$_2$)$_3$ | S | O | |
| 129 | CONH-Me | CH$_2$ | Me | Et | CHO | n-Bu | H | 2,3-(CH$_2$CH$_2$—OCH$_2$CH$_2$) | CH$_2$ | O | |
| 130 | CF=CH-Me | CH$_2$ | Me | c-Pr | COOMe | t-Bu | H | 2,3-(CH$_2$)$_4$ | CHMe | O | |
| 131 | NO$_2$ | CH$_2$ | Me | Morpholino | CH$_2$C≡C—CF$_3$ | CN | H | 4-Morpholino | CH—CH$_2$—C≡CH | CH$_2$ | |
| 132 | CH$_2$OMe | CH$_2$ | Me | NH$_2$ | COCH$_3$ | NMe$_2$ | H | 2,3-(CH$_3$)$_5$ | CH—CH$_2$—COOMe | CHMe | |
| 133 | OPh | CHMe—CHMe | Me | NMe$_2$ | CO-c-Pr | COOMe | H | 2,3-(CH$_2$)$_3$ | CCl$_2$ | CH$_2$ | |
| 134 | OCH$_2$—C≡CH | CH$_2$ | Me | H | CH$_2$NMe$_2$ | COMe | H | 3,4-(CH$_2$)$_3$ | CF$_2$ | CHMe | |
| 135 | SOMe | CH$_2$ | Me | Me | CH$_2$CH$_2$—NMe$_2$ | CH$_2$Ph | H | 3,4-(CH$_2$CH$_2$—OCH$_2$CH$_2$) | CFCl | CH$_2$ | |
| 136 | SO$_2$Me | CH$_2$ | Me | Et | CH$_2$-piperidine | CH=CH—CH$_3$ | H | 3,4-(CH$_2$)$_4$ | CHCN | CHMe | |
| 137 | F | CH$_2$ | Me | c-Pr | CH$_2$CH$_2$-piperidine | Et | H | 4-CH$_2$Ph | CH$_2$ | CH$_2$ | |
| 138 | OCH$_2$Ph | CH$_2$ | Me | Morpholino | CH$_2$C≡C—CH$_2$-piperidine | H | H | 3-OPh | CHMe | CHMe | |
| 139 | OCOPh | CH$_2$ | Me | NMe$_2$ | CH$_2$COO-Me | CH=CH—CH$_3$ | H | 4-COOMe | S | NMe | |
| 140 | OSO$_2$O-Me | CH$_2$ | Me | NMe$_2$ | CH$_2$CH$_2$—NO$_2$ | CN | H | 2,3,4,5-Me$_4$ | O | NEt | |
| 141 | S—CH—NMePh | CH$_2$ | Me | H | CH$_2$Ph | CH$_2$CH$_2$—NMe$_2$ | H | 3,5-(CF$_3$)$_2$ | O | NH | |
| 142 | O-(4-F-Ph) | CH$_2$ | Me | Me | CH$_2$CH$_2$Ph | CH=CH—CH$_3$ | H | 4-OCF$_3$ | O | O | |
| 143 | OPr | CH$_2$ | Me | Et | CH$_2$—(4-F-Ph) | SCN | Me | 3-t-Bu | O | O | |
| 144 | ONMe$_2$ | CH$_2$ | Me | c-Pr | CH=CH—CH$_3$ | CH$_2$CN | Et | 3-OCF$_3$ | O | O | |
| 145 | NMe-CO-Me | CH$_2$ | Me | Morpholino | CH$_2$-morpholine | H | Pr | 4-t-Bu | O | O | |
| 146 | CH$_2$-t-Bu | CH$_2$ | Me | NH$_2$ | NHMe | CH$_2$C≡C—CH$_2$-piperidine | n-Bu | 4-CH$_2$OMe | O | O | |
| 147 | i-Pr | CH$_2$ | Me | NMe$_2$ | NMe$_2$ | CH$_2$OMe | t-Bu | 4-CH$_2$CF$_3$ | O | O | |
| 148 | NHCOPh | CH$_2$ | Me | H | CH$_2$CH$_2$OH | Me | CN | 4-COMe | CH$_2$ | O | |
| 149 | NMePh | CH$_2$ | Me | Me | CH$_2$CH$_2$O-Me | Et | NMe$_2$ | 4-CONMe$_2$ | CMe$_2$ | O | |
| 150 | NHCOPh | CH$_2$ | Me | Et | CH$_2$CH$_2$O-Et | Pr | COOMe | 4-CONHMe | O | CMe$_2$ | |
| 151 | C≡CMe | CHCF$_3$ | Me | c-Pr | CH$_2$CH$_2$O-Ph | n-Bu | COMe | 4-CONH$_2$ | N-CH$_2$—C≡CH | O | |
| 152 | SCN | CH=CF—CHMe | Me | Morpholino | CH$_2$CH$_2$—NHPh | t-Bu | CH$_2$Ph | 4-Me | N-COCH$_3$ | CH$_2$ | |
| 153 | CN | CHMe | CF$_3$ | NH$_2$ | CH$_2$CH$_2$—NMePh | CN | CH=CH—CH$_3$ | | O | | |

TABLE 1-continued

Compounds of the formula (I)

$$R^4R^5N \text{-pyrimidine-} C(R^1)(X)(CR^2R^3)_m, \text{ NR}^6\text{—CH(R}^7\text{)—CH(R}^8\text{)—Y—Ph(R}^9)_n \quad (1)$$

| No | $R^1$ | $(CR^2R^3)_m$ | $R^4$ | $R^5$ | $R^6$ | $R^7$ | $R^8$ | $(R^9)_n$ | X | Y | M.p. |
|---|---|---|---|---|---|---|---|---|---|---|---|
| 154 | CONH-Me | CMeEt | $CF_2Cl$ | $NMe_2$ | $CH_2CH_2O$-4-F-Ph | $NMe_2$ | Et | 4-Me, 3-t-Bu | $CH_2$ | $CMe_2$ | |
| 155 | CF=CH-Me | Cyclo-butylene | $CF_2CF_3$ | H | $CH_2CH_2O$-3,5-$Me_2$-Ph | COOMe | H | 4-Me, 3-OCF$_3$ | $CMe_2$ | O | |
| 156 | $NO_2$ | CMeEt | $CH_2CF_3$ | Me | $CH_2CH_2O$-2,3-$Cl_2$-Ph | COMe | CH=CH—$CH_3$ | 3-Me, 4-t-Bu | O | N-Bu | |
| 157 | $CH_2OMe$ | CHOPh | Et | Et | $CH_2CH_2O$-4-CONH$_2$-Ph | $CH_2Ph$ | CN | 3-Me, 4-$CH_2$OMe | CHMe | N-Et | |
| 158 | OPh | CH—SOMe | Pr | c-Pr | $CH_2CH_2$—COOMe | CH=CH—$CH_3$ | $CH_2CH_2$—$NMe_2$ | 3-Me, 4-$CH_2CF_3$ | $CH_2$ | O | |
| 159 | $OCH_2$—C≡CH | CH—COMe | Bu | Morpholino | $CH_2CH_2$—$CONH_2$ | Et | CH=CH—$CH_3$ | 3-Me, 4-COMe | O | S | |
| 160 | SOMe | C(Me)OMe | Ph | $NH_2$ | $CH_2CH_2$—$CONMe_2$ | H | SCN | 3-Me, 4-COOMe | S | $SO_2$ | |
| 161 | $SO_2Me$ | CHC=CMe | 4-F-Ph | $NMe_2$ | $CH_2CH_2$-2-thiophene | CH=CH—$CH_3$ | $CH_2$CN | 3-Me, 4-$CONH_2$ | $CH_2$ | O | |
| 162 | F | CHC=CH | H | H | $CH_2CH_2$-(3-Br-2-thiophene) | CN | H | 3-Me, 4-CONHMe | CHMe | SO | |
| 163 | $OCH_2Ph$ | CHCF=CFCl | H | Me | $CH_2CH_2$-2-pyridine | $CH_2CH_2$—$NMe_2$ | $CH_2$C≡C—$CH_2$-piperidine | 3-Me, 4-$CONH_2$ | $CCl_2$ | $CH_2$ | |
| 164 | OCOPh | CH—NMeEt | Me | Et | $CH_2CH_2$-(3-Cl-2-pyridine) | CH=CH—$CH_3$ | $CH_2$OMe | 4,5-$Me_2$, 3-t-Bu | $CH_2$—$CH_2$—COOMe | CHMe | |
| 165 | $OSO_2$—O-Me | CH—NMeCH$_2$O-Me | Bu | c-Pr | $CH_2CH_2$-(3-Cl-5-$F_3$C-2-pyridine) | SCN | Me | 4,5-$Me_2$, 3-$OCF_3$ | $CF_2$ | $CH_2$ | |
| 166 | S—CHMe-Ph | CMe-COOMe | $CF_3$ | Morpholino | Me | $CH_2$CN | Et | 3,5-$Me_2$, 4-t-Bu | $CF_2$ | CHMe | |
| 167 | O-(4-F-Ph) | CH—CONHMe | $CF_2Cl$ | $NH_2$ | Bu | H | H | 3,5-$Me_2$, 4-$CH_2$OMe | CFCl | $CH_2$ | |
| 168 | OEt | CH—NHCOPh | $CF_2CF_3$ | $NMe_2$ | i-Pr | $CH_2$C≡C—$CH_2$-piperidine | H | 3,5-$Me_2$, 4-$CH_2CF_3$ | CHCN | CHMe | |
| 169 | $ONMe_2$ | CMe-NH-t-Bu | $CH_2CF_3$ | H | $CH_2$—(4-Me-Ph) | $CH_2$OMe | H | 3,5-$Me_2$, 4-COMe | $CH_2$ | $CH_2$ | |

TABLE 1-continued

Compounds of the formula (I)

$$R^1\underset{C}{\overset{X}{|}}(CR^2R^3)_m \quad \text{pyrimidine with } R^4R^2N \text{ and } NR^6-CH(R^7)-CH(R^8)-Y-\text{Ph}(R^9)_n \quad (1)$$

| No | R¹ | (CR²R³)ₘ | R⁴ | R⁵ | R⁶ | R⁷ | R⁸ | (R⁹)ₙ | X | Y | M.p. |
|---|---|---|---|---|---|---|---|---|---|---|---|
| 170 | NMe-CO-Me | CH—OSO₂Me | Et | Me | NH₂ | | CH₂OCH₂ | 3,5-Me₂ | CHMe | CHMe | |
| 171 | CH₂—t-Bu | CHCOPh | Pr | Et | CH₂C≡CH | | CH₂CH₂CH₂ | 4-COOMe | S | NMe | |
| 172 | i-Pr | CHSMe | Bu | c-Pr | CH₂CN | | CH₂CH₂CH₂ | 3,5-Me₂ | O | NEt | |
| 173 | NHCOPh | CHOPh | Ph | Morpholino | CHO | | CH₂SCH₂ | 4-CONMe₂ | O | NH | |
| 174 | NMePh | CH—CH₂OMe | 4-F-Ph | NH₂ | COOMe | | CH₂NMe-CH₂ | 4-CONHMe | O | O | |
| 175 | NHCOPh | CMe-c-Pr | H | NMe₂ | CH₂—CF₃ | | CH₂N(CH₂Ph)-CH₂ | 3,5-Me₂ | O | O | |
| 176 | NH-c-Pr | CMe-SO₂OMe | H | NHPh | COCH₃ | | CH₂CHMe-CH₂ | 3,5-(OMe)₂ | O | O | |
| 177 | C≡CMe | CH₂ | Me | NHCH₂—CH₂OMe | CO-c-Pr | | CH—CHNO₂—CH₂ | 3,5-Me₂ | O | O | |
| 178 | SCN | CH₂ | Bu | CH₂CH₂—OMe | CH₂NMe₂ | | CH=CH—CH₂CH₂ | 3,5-Me₂ | O | O | |
| 179 | CN | CH₂ | CF₃ | CH₂CH₂—SMe | CH₂CH₂—NMe₂ | | CH₂CH₂—CH=CH | 3,5-Me₂ | O | O | |
| 180 | CONH-Me | CH₂ | CF₂Cl | COMe | CH₂-piperidine | | CH₂CH₂—CHCH₂ | 3,5-Me₂ | CH₂ | O | |
| 181 | CF=CH-Me | CH₂ | CF₂CF₃ | COPh | CH₂CH₂-piperidine | | CONMe-CO | 3,5-Me₂ | CMe₂ | CMe₂ | |
| 182 | NO₂ | CH₂ | CH₂CF₃ | H | CH₂C≡C—CH₂-piperidine | | CH₂OCH₂ | 3,5-Me₂ | O | O | |
| 183 | CH₂OMe | CH₂ | Et | Me | CH₂COO-Me | | CH₂CH₂CH₂ | 3,5-Me₂ | N—CH₂—C≡CH | O | |
| 184 | OPh | CH₂ | Pr | Et | CH₂CH₂—NO₂ | | CH₂CH₂CH₂ | 2,4-Me₂ | N—COCH₃ | O | |
| 185 | OCH₂—C≡CH | CH₂ | Bu | c-Pr | CH₂Ph | | CH₂SCH₂ | 2,4-Me₂ | O | CH₂ | |
| 186 | SOMe | CH₂ | Ph | Morpholino | CH₂CH₂Ph | | CH₂NMe-CH₂ | 2,4-Me₂ | CH₂ | CMe₂ | |
| 187 | SO₂Me | CH₂ | 4-F-Ph | NH₂ | CH₂—(4-F-Ph) | | CH₂N(CH₂Ph)-CH₂ | 2,4-Me₂ | CMe₂ | O | |
| 188 | F | CH₂ | H | NMe₂ | CH=CH—CH₃ | | CH₂CHMeCH₂ | 2,4-Me₂ | O | NPr | |
| 189 | OCH₂Ph | CH₂ | H | H | CH₂-morpholine | | CH₂CH(NH₂)CH₂ | 2,4-Me₂ | CHMe | N(O) | |
| 190 | OCOPh | CH₂ | Me | Me | NHMe | | CH=CH—CH₂CH₂ | 2,4-Me₂ | CH₂O | O | |
| 191 | OSO₂-O-Me | CH₂ | Bu | Et | NMe₂ | | CH=CH—CH=CH | 2,4-Me₂ | S | O | |
| 192 | SCHMe-Ph | CH₂ | CF₃ | c-Pr | CH₂CH₂OH | | CH₂CH—CHCH₂ | 2,4-Me₂ | CH₂ | O | |
| 193 | O-(4-F-Ph) | CH₂CH₂ | CF₂Cl | Morpholino | CH₂CH₂-O-Me | | CONMe-CO | 2,4-Me₂ | CHMe | CH₂ | |
| 194 | O | CH₂CH₂CH₂ | CF₂CF₃ | NH₂ | CH₂CH₂O-Et | H | Et | 3,4-(OMe)₂ | CH(CH₂—C≡CH) | CMe₂ | |
| 195 | ONMe₂ | CH₂ | CF₂CF₃ | NMe₂ | CH₂CH₂O-Ph | H | Me | 3,4-(OMe)₂ | CH(CH₂—COOMe) | CHMe | |
| 196 | NMeCO-Me | CH₂ | Et | H | CH₂CH₂—NHPh | H | Bu | 3,4-(OMe)₂ | CCl₂ | CH₂ | |
| 197 | CH₂-t-Bu | CH₂ | Pr | Me | CH₂CH₂—NMePh | H | CN | 3-OMe, | | CH₂ | |

TABLE 1-continued

Compounds of the formula (I)

$$R^4R^5N\underset{N}{\overset{N}{\diagdown}}\underset{}{\underset{}{\bigcirc}}\underset{N}{\overset{N}{\diagup}}NR^6-CH(R^7)-CH(R^8)-Y-\text{Ph}(R^9)_n \quad R^1-C(X)-(CR^2R^3)_m- \quad (1)$$

| No | R¹ | (CR²R³)ₘ | R⁴ | R⁵ | R⁶ | R⁷ | R⁸ | (R⁹)ₙ | X | Y | M.p. |
|---|---|---|---|---|---|---|---|---|---|---|---|
| 198 | i-Pr | CH₂ | Bu | Et | CH₂CH₂O-(4-F-Ph) | H | SCN | 5-Me | CF₂ | CHMe | |
| 199 | NHCOPh | CH₂ | Ph | c-Pr | CH₂CH₂O-(3,5-Me₂-Ph) | H | NMe₂ | 3-OMe, 5-Me | CFCl | CH₂ | |
| 200 | NMePh | CH₂ | 4-F-Ph | Morpholino | CH₂CH₂O-(2,3-Cl₂-Ph) | H | CH₂NMe₂ | 3-SMe, 5-Me | CHCN | CHMe | |
| 201 | NHCOPh | CH₂ | H | NH₂ | CH₂CH₂O-(4-CONH₂-Ph) | H | CH₂NHPh | 3-SMe, 5-Cl | CH₂ | CH₂ | |
| 202 | C≡CMe | CHCF₃ | H | NMe₂ | CH₂CH₂—COOMe | H | CHMe-NMe₂ | 3-SMe, 5-NO₂ | CHMe | CHMe | |
| 203 | SCN | CHCF=CHMe | Me | H | CH₂CH₂—CONH₂ | H | COPh | 3-CF₂CF₂H | S | NMe | |
| 204 | CN | CHMe | Bu | Me | CH₂CH₂—CONMe₂ | H | H | 3-CF₂CF₂H, 5-Me | O | NEt | |
| 205 | CONH-Me | CMeEt | H | Et | CH₂CH₂-2-thiophene | H | COMe | 3-CF₃, 5-Me | O | NH | |
| 206 | CF=CH-Me | Cyclobutylene | H | c-Pr | CH₂CH₂-(3-Br-2-thiophene) | H | Et | 3-CF₃, 5-Me | O | O | |
| 207 | NO₂ | CMeEt | H | Morpholino | CH₂CH₂-2-pyridine | H | 2-Pyridyl | 3-SMe, 5-F | O | O | |
| 208 | CH₂OMe | CHOPh | H | NH₂ | CH₂CH₂-(3-Cl-2-pyridine) | H | 2-Thio-phenyl | 3-SMe, 5-NO₂ | O | O | |
| 209 | OPh | CHSOMe | H | NMe₂ | CH₂CH₂-(3-Cl-5-F₃C-2-pyridine) | H | H | 3-CF₂CF₂H | O | O | |
| 210 | OCH₂—C≡CH | CHCOMe | H | H | Me | H | H | 3-CF₂CF₂H, 5-OMe | O | O | |
| 211 | SOMe | CMe-OMe | H | Me | Bu | H | Me | 3-CF₃, 5-OMe | O | O | |
| 212 | SO₂Me | CHC≡CMe | H | Et | i-Pr | H | Et | 3-CF₃, 5-Me | O | O | |
| 213 | F | CHC≡CH | H | c-Pr | CH₂-(4-Me-Ph) | H | Pr | 4-OCH₂—C≡CH | CMe₂ | O | |
| 214 | OCH₂Ph | CHCF=CFCl | H | Morpholino | CH₂CH₂-(4-t-Bu-Ph) | H | Bu | 3-OCH₂—C≡CH | O | CMe₂ | |

TABLE 1-continued

Compounds of the formula (I)

$$R^4R^2N - \overset{\overset{R^1}{\underset{\underset{C}{|}}{C}}}{\underset{N}{\overset{X}{\underset{|}{C}}}} \overset{(CR^2R^3)_m}{\underset{N}{\overset{}{}}} NR^6 - CH - CH - Y \overset{R^7}{\underset{R^8}{\overset{}{\phantom{-}}}} \overset{(R^9)_n}{\phantom{-}}$$ (1)

| No | R¹ | (CR²R³)ₘ | R⁴ | R⁵ | R⁶ | R⁷ | R⁸ | (R⁹)ₙ | X | Y | M.p. |
|---|---|---|---|---|---|---|---|---|---|---|---|
| 215 | OCOPh | CHNMeEt | Me | NH₂ | CH₂CH₂-(4-Me-Ph) | H | H | 4-OCH₂—C≡CPh | NCH₂—CH=CH | O | |
| 216 | OSO₂O-Me | CH—NMe-CH₂O-Me | H | NMe₂ | CH₂CF₃ | H | H | 4-OCH₂—C≡CCH₃ | N—COCH₃ | O | |
| 217 | SCHMe-Ph | CMe-COOMe | H | H | CF₂CF₂H | H | Me | 3,5-Me₂, 4-CS—SMe | O | CH₂ | |
| 218 | O(4-F-Ph) | CH—CONHMe | H | Me | —S—CCl₃ | H | Et | 3,5-Me₂, 4-CS-OMe | CH₂ | CMe₂ | |
| 219 | OMe | CH—NHCOPh | H | Et | COPh | H | Pr | 3,5-Me₂, 4-CO-SMe | CMe₂ | O | |
| 220 | ONMe₂ | CMe-NH-t-Bu | H | c-Pr | COCH₂Ph | Me | Bu | 3,5-Me₂, 4-SO₂Me | O | NMe | |
| 221 | NMeCO-Me | CH—OSO₂Me | H | Morpholino | CH₂CH₂O-(4-CONH₂-Ph) | Et | H | 3,4-Me₂, 5-SO₃Me | CHMe | NCH₃ | |
| 222 | CH₂-t-Bu | CH—COPh | H | NH₂ | CH₂CH₂—COOMe | Pr | H | 3,5-Me₂, 4-OPh | O | O | |
| 223 | i-Pr | CH—SMe | H | NMe₂ | CH₂CH₂—CONH₂ | Bu | Me | 3,5-Me₂, 4-C≡CPh | CH₂ | CH₂ | |
| 224 | NHCOPh | CH—OPh | H | H | CH₂CH₂-2-thiophene | H | Et | 3,5-Me₂, 4-C≡CH | CH₂ | O | |
| 225 | NMePh | CH—CH₂OMe | H | Me | CH₂CH₂-2-thiophene | H | Pr | 3,5-Me₂, 4-C≡CMe | CH₂ | O | |
| 226 | NHCOPh | CMe-c-Pr | H | Et | CH₂CH₂-(3-Br-2-thiophene | Me | Bu | 3,5-(C≡CH)₂ | CMeCOO-Me | CH₂ | |
| 227 | NH-c-Pr | CMeSO₂OMe | H | c-Pr | CH₂CH₂-2-pyridine | Et | CN | 3,5-(C=CMe₂)₂ | CHCONH-Me | CMe₂ | |
| 228 | F | Cyclobutylene | H | Morpholino | CH₂CH₂-(3-Cl-pyridine) | Pr | SCN | 2-CH₂-t-Bu | CHNHCO-Ph | O | |
| 229 | Cl | CMeEt | H | NH₂ | CH₂CH₂-(3-Cl-5-F₃C-2-pyridine) | Bu | NMe₂ | 3-i-Pr | CMeNH-t-Bu | O | |
| 230 | Br | CHOPh | H | NMe₂ | Me | H | CH₂NMe₂ | 4-NHCOPh | CHOSO₂-Me | CH₂ | |
| 231 | CF₃ | CHSOMe | H | NHPh | Bu | Ph | Et | 4-NMePh | CHCOPh | CMe₂ | |
| 232 | CF₂CF₂H | CHCOMe | Bu | NHCH₂—CH₂OMe | i-Pr | Me | Pr | 4-NHCOPh | CHSMe | O | |

TABLE 1-continued

Compounds of the formula (I)

$$R^4R^2N \text{ pyrimidine with } R^1, X, (CR^2R^3)_m, NR^6-CH(R^7)-CH(R^8)-Y-\text{phenyl}(R^9)_n \text{ (1)}$$

| No | $R^1$ | $(CR^2R^3)_m$ | $R^4$ | $R^5$ | $R^6$ | $R^7$ | $R^8$ | $(R^9)_n$ | X | Y | M.p. |
|---|---|---|---|---|---|---|---|---|---|---|---|
| 233 | CO-c-Pr | CMeOMe | c-Pr | CH$_2$CH$_2$—OMe | CH$_2$-4-Me-Ph | Et | Bu | 3-NH-c-Pr | CHOPh | O | |
| 234 | CONMe$_2$ | CHCOCMe | Et | CH$_2$CH$_2$—SMe | CH$_2$CH$_2$-4-t-Bu-Ph | Pr | CN | 3,5-F | CHCH$_2$O—Me | CH$_2$ | |
| 235 | NMe-c-Pr | CHC≡CH | H | COMe | CH$_2$CH$_2$-4-Me-Ph | Bu | SCN | 4-CH$_2$CH$_2$—OH | CMe-c-Pr | CMe$_2$ | |
| 236 | NH-c-Pr | CHCF=CFCl | H | COPh | CF$_2$CF$_3$ | H | NMe$_2$ | 4-CH$_2$CH$_2$—COOMe | CMeSO$_2$—OMe | O | |
| 237 | S-c-Pr | CHNMeEt | Piperidino | H | —S—CCl$_3$ | H | CH$_2$NMe$_2$ | 4-CH$_2$CH$_2$—CONH$_2$ | CH$_2$ | O | |
| 238 | CH=CMe-c-Pr | CHNMeCH$_2$—OMe | Morpholino | Me | | Me | Ph | 4-CH$_2$CH$_2$—CONMe$_2$ | CH$_2$ | O | |
| 239 | CF=CF-Me | CMeCOOMe | | CH$_2$CH$_2$CH$_2$CH$_2$ | COPh | Et | 4-F-Ph | 3-(CH$_2$CH$_2$-2-thiophene) | CMeCOO-Me | O | |
| 240 | C(Me)=CMe$_2$ | CHCONHMe | | CH$_2$CH$_2$CH$_2$CH$_2$ | COCH$_2$Ph | Pr | 2,4-Cl$_2$-Ph | 4-[CH$_2$CH$_2$-(3-Br-2-thiophene)] | CHCONH-Me | O | |
| 241 | SH | CHNHCOPh | | CH$_2$CH$_2$CH$_2$ | CH$_2$-c-Pr | Bu | Et | 3-(CH$_2$CH$_2$-2-pyridine) | CHNHCO-Ph | O | |
| 242 | OH | CMeNH-t-Bu | | CH$_2$CH$_2$OCH$_2$CH$_2$ | NMe$_2$ | H | Pr | 3-(CH$_2$CH$_2$-2-pyridine) | CMeNH-t-Bu | O | |
| 243 | COOH | CHOSO$_2$Me | | CH$_2$CH$_2$CH$_2$CH$_2$ | CH$_2$CH$_2$—NMe$_2$ | H | Bu | 4-[CH$_2$CH$_2$-2-(3-Cl-5-CF$_3$-2-pyridine)] | CHOSO$_2$-Me | CMe$_2$ | |
| 244 | CONH$_2$ | CHCOPh | Morpholino | Me | CH$_2$CO—CH$_2$NMe$_2$ | Me | CN | 2-Me | CHCOPh | O | |
| 245 | NHCHO | CHSMe | | CH$_2$CH$_2$CH$_2$CH$_2$ | COCH$_2$Ph | Et | SCN | 3-Bu, 4-Me, 5-F | CHSMe | O | |
| 246 | NMe-CHO | CHOPh | | CH$_2$CH$_2$CH$_2$CH$_2$ | CH$_2$-c-Pr | Pr | NMe$_2$ | 3,5-(i-Pr)$_2$ | CHOPh | CH$_2$ | |
| 247 | SO$_2$OH | CHCH$_2$OMe | | CH$_2$CH$_2$CH$_2$CH$_2$ | NMe$_2$ | Bu | CH$_2$NMe$_2$ | 3,5-Me$_2$ | CHCH$_2$O—Me | CMe$_2$ | |
| 248 | OSO$_2$—OMe | CMe-c-Pr | | CH$_2$CH$_2$OCH$_2$CH$_2$ | CH$_2$CH$_2$—NMe$_2$ | H | CH$_2$NHPh | 3,5-Me$_2$ | CMe-c-Pr | O | |
| 249 | O—NMeEt | CMe-SO$_2$OMe | | CH$_2$CH$_2$CH$_2$CH$_2$ | CH$_2$CO—CH$_2$NMe$_2$ | H | CHMe-NMe$_2$ | 3,5-Me$_2$ | O | N-Bu | 71–73 |
| 250 | H | CH—CH$_3$ | H | H | H | CH$_3$ | H | 4-Cl | O | O | 171–173 |
| 251 | Ph | CH$_2$ | H | H | H | CH$_3$ | H | 3,5-Me$_2$ | CH$_2$ | O | |
| 252 | CH$_3$ | CH$_2$ | H | H | H | CH$_3$ | H | 4-Cl | O | O | |

TABLE 1-continued

Compounds of the formula (I)

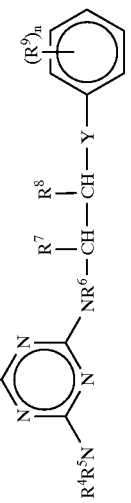

| No | R¹ | (CR²R³)$_m$ | R⁴ | R⁵ | R⁶ | R⁷ | R⁸ | (R⁹)$_n$ | X | Y | M.p. |
|---|---|---|---|---|---|---|---|---|---|---|---|
| 253 | H | CH—CH$_3$ | H | H | H | CH$_3$ | H | 3,5-Me$_2$ | O | O | 61–63 |
| 254 | CH$_3$ | CH—CH$_3$ | H | H | H | CH$_3$ | H | 3,5-Me$_2$, 4-Cl | O | S | liquid |
| 255 | H | CMe$_2$ | H | H | H | CH$_3$ | H | 3,5-Me$_2$, 4-Cl | O | O | liquid |
| 256 | H | CH$_2$—CH$_2$—CH$_2$ | H | H | H | H | H | 2,4-Me$_2$ | CH$_2$ | O | liquid |
| 257 | Me | CH$_2$ | H | H | H | H | H | 2,4-Me$_2$ | CH$_2$ | O | liquid |
| 258 | OH | CH$_2$ | H | H | H | Me | H | 3,5-Me$_2$ | CH$_2$ | O | liquid |
| 259 | Me | CH$_2$ | H | H | H | Me | H | H | CH$_2$ | CH$_2$ | liquid |
| 260 | H | CH$_2$ | H | H | H | Me | H | H | CH$_2$ | CH$_2$ | liquid |
| 261 | Me | CH$_2$ | H | H | H | Me | H | 3,4-Me$_2$, 4-I | CH$_2$ | O | liquid |
| 262 | Me | CH$_2$ | H | H | H | Me | H | 3,4-Cl | CH$_2$ | O | 108–110 |
| 263 | Me | CH$_2$ | H | H | H | Me | H | 3-Me, 5-iPr | CH$_2$ | O | liquid |
| 264 | Me | CH$_2$ | H | H | H | Me | H | 3,5-Me$_2$ | CH$_2$ | CH$_2$ | liquid |
| 265 | Me | CH$_2$ | H | H | H | Et | H | 3,5-Me$_2$ | CH$_2$ | CH$_2$ | 50–52 |
| 266 | Me | CH$_2$ | H | H | H | i-Pr | H | 3,5-Me$_2$ | CH$_2$ | CH$_2$ | liquid |
| 267 | F | CH$_2$ | H | H | H | Me | H | H | CH$_2$ | CH$_2$ | solid |
| 268 | F | CH$_2$ | H | H | H | Et | H | H | CH$_2$ | O | liquid |
| 269 | H | CH$_2$CH$_2$CH$_2$ | H | H | H | Me | H | 2,3-Me$_2$ | CH$_2$ | O | solid |
| 270 | H | CH$_2$ | H | H | H | Me | H | 2,3-Me$_2$ | CH$_2$ | O | solid |
| 271 | Me | CH$_2$ | H | H | H | Me | Me | 3,5-Me | CH$_2$ | O | 55–60 |
| 272 | Me | CH$_2$ | H | H | H | H | —CH$_2$—CH$_2$—CH$_2$— | 3,5-Me | CH$_2$ | O | liquid |
| 273 | Me | CH$_2$ | H | H | H | Me | Me | 3,5-Me | CH$_2$ | O | liquid |
| 274 | Me | CH$_2$—CH$_2$ | H | H | H | Me | H | 3-Me | CH$_2$ | O | liquid |
| 275 | Me | CH$_2$—CH$_2$ | H | H | H | Et | H | 3,5-Me$_2$ | CH$_2$ | O | liquid |
| 276 | Me | CH$_2$—CH$_2$ | H | H | H | Me | H | 3,5-Me$_2$ | CH$_2$ | O | liquid |
| 277 | Et | CH$_2$—CH$_2$ | H | H | H | Me | H | 3,5-Me$_2$ | CH$_2$ | O | liquid |
| 278 | i-Pr | CH$_2$—CH$_2$ | H | H | H | Me | H | 3,5-(OMe)$_2$ | CH$_2$ | O | liquid |
| 279 | Me | CH$_2$ | H | H | H | Me | H | 3,5-(OMe)$_2$ | CH$_2$ | O | liquid |
| 280 | Me | CH$_2$ | H | H | H | Et | H | 3,5-Me$_2$ | CH$_2$ | O | liquid |
| 281 | Me | CH$_2$ | H | H | H | Et | H | 3,5-Me$_2$ | CH$_2$ | O | liquid |
| 282 | Me | CH$_2$ | H | H | H | Me | H | 3-Me, 5-OMe | CH$_2$ | O | liquid |
| 283 | Me | CH$_2$—CH$_2$ | H | H | H | Me | H | H | CH$_2$ | CH$_2$ | liquid |

TABLE 1-continued
Compounds of the formula (I)
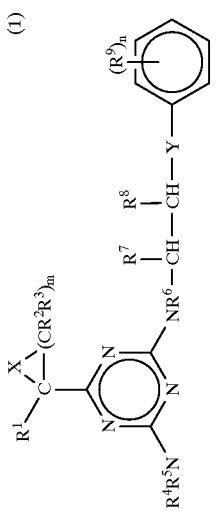
| No | $R^1$ | $(CR^2R^3)_m$ | $R^4$ | $R^5$ | $R^6$ | $R^7$ | $R^8$ | $(R^9)_n$ | X | Y | M.p. |
|---|---|---|---|---|---|---|---|---|---|---|---|
| 284 | Me | $CH_2$—$CH_2$ | H | H | H | Me | H | 3,5-$(OMe)_2$ | $CH_2$ | O | liquid |
| 285 | Me | $CH_2$ | H | H | H | 2-Thienyl | H | 3,5-$Me_2$ | $CH_2$ | O | 122–124 |
| 286 | Me | $CH_2$ | H | H | H | 3-Cl, 4-F-Ph | H | 3,5-$Me_2$ | $CH_2$ | O | 127–128 |
| 287 | Me | $CH_2$ | H | H | H | 3-Me-Ph | H | 3,5-$Me_2$ | $CH_2$ | O | |
| 288 | Me | $CH_2$ | H | H | H | Me | H | 3-Br | $CH_2$ | O | |
| 289 | Me | $CH_2$ | H | H | H | Me | H | 3-Cl | $CH_2$ | O | |
| 290 | Me | $CH_2$ | H | H | H | Me | H | 3-Et | $CH_2$ | O | |

B. FORMULATION EXAMPLES a) A dusting agent is obtained by mixing 10 parts by weight of a compound of the formula (I) and 90 parts by weight of talc as inert substance and comminuting the mixture in a hammer mill.

b) A readily water-dispersible wettable powder is obtained by mixing 25 parts by weight of a compound of the formula (I), 64 parts by weight of kaolin-containing quartz as inert material, 10 parts by weight of potassium ligninsulfonate and 1 part by weight of sodium oleoylmethyltaurinate as wetting agent and dispersant and grinding the mixture in a pinned-disk mill.

c) A readily water-dispersible dispersion concentrate is obtained by mixing 20 parts by weight of a compound of the formula (I) and 6 parts by weight of alkylphenol polyglycol ether (®Triton X 207), 3 parts by weight of isotridecanol polyglycol ether (8 EO) and 71 parts by weight of paraffinic mineral oil (boiling range for example from about 255 to over 277° C.) and grinding the mixture in a ball mill to a fineness below 5 microns.

d) An emulsifiable concentrate is obtained from 15 parts by weight of a compound of the formula (I), 75 parts by weight of cyclohexanone as solvent and 10 parts by weight of ethoxylated nonylphenol as emulsifier.

e) Water-dispersible granules are obtained by mixing 75 parts by weight of a compound of the formula (I), 10 parts by weight of calcium ligninsulfonate 5 parts by weight of sodium lauryl sulfate 3 parts by weight of polyvinyl alcohol and 7 parts by weight of kaolin,
grinding the mixture in a pinned-disk mill and granulating the powder in a fluidized bed by spraying on water as granulation liquid.

f) Water-dispersible granules are also obtained by homogenizing and precomminuting 25 parts by weight of a compound of the formula (I), 5 parts by weight of sodium 2,2'-dinaphthylmethane-6,6'-disulfonate 2 parts by weight of sodium oleoylmethyltaurinate 1 part by weight of polyvinyl alcohol 17 parts by weight of calcium carbonate and 50 parts by weight of water,
in a colloid mill, followed by grinding in a bead mill, and atomizing and drying the resulting suspension in a spray tower, using a single-substance nozzle.

C. BIOLOGICAL EXAMPLES

1. Pre-emergence action against weeds

Seeds or rhizome pieces of monocotyledon or dicotyledon weed plants are placed in sandy loam soil in plastic pots and covered with soil. The novel compounds, formulated as wettable powders or emulsion concentrates, are then applied to the surface of the soil cover in the form of an aqueous suspension or emulsion at an application rate of from 600 to 800 l of water/ha (converted), in various dosages.

After the treatment, the pots are placed in a greenhouse and kept under good growth conditions for the weeds. After the test plants have emerged, the damage to the plants or the negative effect on emergence is rated visually by comparison with untreated controls. As shown by the test results, the novel compounds have a good herbicidal pre-emergence activity against a broad spectrum of gramineous and broad-leaved weeds. For example, the Examples Nos. 1, 3, 4, 5, 6, 7, 12, 13, 19, 25, 27, 29, 32, 37, 39, 40, 49, 50, 64, 68, 73, 74, 82, 84, 85, 88, 92, 96, 101, 102, 103, 104, 106, 107, 108, 109, 110, 250, 251, 253, 256, 257, 259, 261, 262, 264, 266, 267, 269, 270, 271, 272, 273, 274, 275, 280, 281, 282, 283, 284, 285 and 286 (see Table 1) in the test have a very good herbicidal action against weeds such as *Sinapis alba, Chrysanthemum segetum, Avena sativa, Stellaria media, Echinochloa crus-galli, Lolium multiflorum,* Setaria spp., *Abutilon theophrasti, Amaranthus retroflexus* and *Paricum miliaceum* when applied pre-emergence at a rate of 0.5 kg or less of active substance per hectare.

2. Post-emergence action against weeds

Seeds or rhizome pieces of monocotyledon or dicotyledon weeds are placed in sandy loam soil in plastic pots, covered with soil and cultivated in a greenhouse under good growth conditions. Three weeks after sowing, the test plants are treated at the three-leaf stage. The novel compounds, formulated as wettable powders or emulsion concentrates, are then sprayed in various dosages onto the green parts of the plants at an application rate of from 600 to 800 l of water/ha (converted), and, after the test plants have remained in the greenhouse for about 3 to 4 weeks under optimum growth conditions, the action of the preparations is rated visually in comparison to untreated controls. The novel compositions also have a good post-emergence herbicidal activity against a broad spectrum of economically important gramineous and broad-leaved weeds. For example, Examples Nos. 1, 3, 4, 5, 6, 7, 12, 13, 19, 25, 27, 29, 32, 37, 39, 40, 49, 50, 64, 68, 73, 74, 82, 84, 85, 88, 92, 96, 101, 102, 103, 104, 106, 107, 108, 109, 110, 250, 251, 253, 256, 257, 259, 261, 264, 266, 267, 269, 270, 271, 272, 273, 274, 275, 280, 281, 282, 283, 284, 285 and 286 (see Table 1) show a very good herbicidal action in the test against harmful plants such as *Sinapis alba, Echinochloa crus-galli, Lolium multiflorum, Chrysanthemum segetum,* Setaria spp., *Abutilon theophrasti, Amaranthus retroflexus, Paricum miliaceum* and *Avena sativa* when applied post-emergence at a rate of 0.5 kg or less of active substance per hectare.

3. Action on weeds in rice

Transplanted and sown rice and also typical rice weeds are cultivated in closed plastic pots in a greenhouse to the three-leaf stage (Echinochloa 1.5-leaf) under paddy rice conditions (dammed height of water: 2–3 cm). This is followed by treatment with the novel compounds. For this purpose the formulated active compounds are suspended, dissolved or emulsified in water and applied by pouring them into the dammed water around the test plants in different dosages. After this treatment, the test plants are set up in a greenhouse under optimum growth conditions and are maintained in this way under these conditions throughout the test period.

About three weeks after application, evaluation is made by visual rating of the damage to the plants in comparison with untreated controls, in which case, for example, compounds Nos. 1, 3, 4, 5, 6, 7, 12, 13, 19, 25, 27, 29, 32, 37, 39, 40, 49, 50, 64, 68, 73, 74, 82, 84, 85, 88, 92, 96, 101, 102, 103, 104, 106, 107, 108, 109, 110, 250, 251, 253, 256, 257, 259, 261, 262, 264, 266, 267, 269, 270, 271, 272, 273, 274, 275, 280, 281, 282, 283, 284, 285 and 286 (see Table 1) show a very good herbicidal action against weeds which are typical of rice crops, for example *Cyperus monti, Echinochloa crus-galli, Eleocharis acicularis* and *Sagittaria pygmaea.*

4. Tolerance by crop plants

In further greenhouse experiments, seeds of a relatively large number of crop plants and weeds are placed in sandy loam soil and covered with soil. Some of the pots are treated immediately as described under Section 1, while the remainder are placed in a greenhouse until the plants have developed two to three true leaves, and then sprayed with various dosages of the novel substances of the formula (I), as described in Section 2. Four to five weeks after the application, and after the plants have remained in the greenhouse, visual rating shows that the novel compounds leave dicotyledon crops such as, for example, soya, cotton, oil seed rape, sugar beet and potatoes undamaged when employed pre- and post-emergence, even when high dosages of active compound are used. Moreover, some substances also leave gramineous crops unharmed, for example barley, wheat, rye, Sorghum species, maize or rice. Some of the compounds of the formula (I) display a high selectivity and are therefore suitable for controlling unwanted plant growth in agricultural crops.

We claim:

1. A compound of the formula (I) or salt thereof,

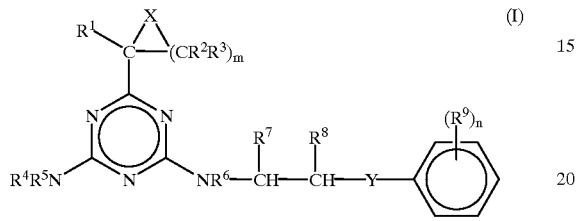

in which $R^1$, $R^2$ and $R^3$ independently of one another are hydrogen, halogen, hydroxyl, amino, nitro, formyl, carboxyl, cyano, thiocyanato, $(C_1-C_4)$alkyl, cyano-$(C_1-C_4)$alkyl, $(C_1-C_4)$alkoxy, $(C_1-C_4)$alkylamino, di-[$(C_1-C_4)$alkyl]-amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-[$(C_1-C_4)$alkyl]-amino-$(C_1-C_4)$alkyl, $(C_3-C_9)$-cycloalkylamino-$(C_1-C_4)$alkyl, $(C_3-C_9)$-cycloalkyl, heterocyclyl-$(C_1-C_4)$alkyl having 3 to 9 ring members, the cyclic groups in 3 latter radicals being unsubstituted or substituted by one or more radicals selected from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxy-carbonyl-$(C_1-C_4)$alkyl, $(C_1-C_4)$alkylamino-carbonyl-$(C_1-C_4)$alkyl, $(C_1-C_4)$alkylcarbonyl, $(C_1-C_4)$alkoxy-carbonyl, aminocarbonyl, $(C_1-C_4)$alkylaminocarbonyl, phenoxy-$(C_1-C_4)$alkyl, phenyl-$(C_1-C_4)$alkyl, heterocyclyl, heterocyclyl-amino, heterocyclyloxy, heterocyclylthio, or one of the 16 later radicals which is substituted in the cyclic moiety or in the acyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkyl-carbonyl, $(C_1-C_4)$alkoxy-carbonyl and $(C_1-C_4)$alkoxy, and wherein heterocyclyl is a radical containing in each case 3 to 9 ring atoms and 1 hetero-ring atom selected from the group consisting of N, O, or S or is a radical selected from the group consisting of pyrimidinyl, pyridazinyl, pyrazinyl, thiazolyl, oxazolyl, imidazolyl, piperidyl, piperazinyl, dioxolanyl and morpholinyl, or $R^2$ and $R^3$ together with the carbon atom of the group $CR^2R^3$ are a saturated or partially unsaturated carbocyclic radical having 3 to 6 ring members or heterocyclyl having 3 to 6 ring members where 1 of these ring atoms is a hetero-ring atom selected from the group consisting of O, N and S, or is a radical selected from the group consisting of pyrimidinyl, pyridazinyl, pyrazinyl, thiazolyl, oxazolyl, imidazolyl, piperidyl, piperazinyl, dioxolanyl and morpholinyl, said carbocyclic or heterocyclic radicals being unsubstituted or substituted by one or more radicals selected from the group consisting of $(C_1-C_4)$alkyl, halogen and oxo, $R^4$ and $R^5$ independently of one another are hydrogen, amino, formyl, $(C_1-C_4)$alkyl, cyano$(C_1-C_4)$alkyl, $(C_1-C_4)$alkylamino, di[$(C_1-C_4)$alkyl]-amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkyl-amino-$(C_1-C_4)$alkyl, di-[$(C_1-C_4)$alkyl]-amino-$(C_1-C_4)$alkyl, $(C_3-C_9)$-cycloalkylamino-$(C_1-C_4)$alkyl, $(C_3-C_9)$-cycloalkyl, $(C_3-C_9)$-heterocyclyl-$(C_1-C_4)$alkyl having 3 to 9 ring members, the cyclic groups in the 3 latter radicals being unsubstituted or substituted by one or more radicals selected from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxy-carbonyl-$(C_1-C_4)$alkyl, $(C_1-C_4)$alkylamino-carbonyl-$(C_1-C_4)$alkyl, $(C_1-C_4)$alkylcarbonyl, $(C_1-C_4)$alkoxy-carbonyl, aminocarbonyl, $(C_1-C_4)$alkylamino-carbonyl, phenoxy-$(C_1-C_4)$alkyl, phenyl-$(C_1-C_4)$alkyl, heterocyclyl, heterocyclyl-amino, heterocyclyloxy, heterocyclylthio, or one of the 16 latter radicals which is substituted in the acyclic moiety or in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkyl-carbonyl, $(C_1-C_4)$alkoxy-carbonyl and $(C_1-C_4)$alkoxy, and wherein heterocyclyl is a radical containing in each case 3 to 9 ring atoms and 1 hetero-ring atom selected from the group consisting of N, O and S or is a radical selected from the group consisting of pyrimidinyl, pyridazinyl, pyrazinyl, thiazolyl, oxazolyl, imidazolyl, piperidyl, piperazinyl, dioxolanyl and morpholinyl, or $R^4$ and $R^5$ together with the nitrogen atom of the group $NR^4R^5$, form a heterocyclic radical having 3 to 6 ring atoms and, in addition to N atom, optionally one of these ring atoms is a hetero-ring atom, selected from the group consisting of N, O and S, and said radical are unsubstituted or substituted by one or more radicals selected from the group consisting of halogen, $(C_1-C_4)$alkyl and oxo, $R^6$ is hydrogen, amino, formyl, $(C_1-C_4)$alkyl, cyano $(C_1-C_4)$alkyl, $(C_1-C_4)$alkylamino, di[$(C_1-C_4)$alkyl]-amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkyl-amino-$(C_1-C_4)$alkyl, di-[$(C_1-C_4)$alkyl]-amino-$(C_1-C_4)$alkyl, $(C_3-C_9)$-cycloalkylamino-$(C_1-C_4)$alkyl, $(C_3-C_9)$-cycloalkyl, $(C_3-C_9)$-heterocyclyl-$(C_1-C_4)$alkyl having 3 to 9 ring members, the cyclic groups in the 3 latter radicals being unsubstituted or substituted by one or more radicals selected from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxy-carbonyl-$(C_1-C_4)$alkyl, $(C_1-C_4)$alkylamino-carbonyl-$(C_1-C_4)$alkyl, $(C_1-C_4)$alkylcarbonyl, $(C_1-C_4)$alkoxy-carbonyl, aminocarbonyl, $(C_1-C_4)$alkylamino-carbonyl, phenoxy-$(C_1-C_4)$alkyl, phenyl-$(C_1-C_4)$alkyl, heterocyclyl, heterocyclyl-amino, heterocyclyloxy, heterocyclylthio, or one of the 16 latter radicals which is substituted in the acyclic moiety or in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkyl-carbonyl, $(C_1-C_4)$alkoxy-carbonyl and $(C_1-C_4)$alkoxy, and wherein heterocyclyl is a radical containing in each case 3 to 9 ring atoms and 1 hetero-ring atom selected from the group consisting of N, O and S, or is a radical selected from the group consisting of pyrimidinyl, pyridazinyl, pyrazinyl, thiazolyl, oxazolyl, imidazolyl, piperidyl, piperazinyl, dioxolanyl and morpholinyl, or $R^7$ and $R^8$ independently of one another are hydrogen, halogen, hydroxyl, amino, nitro, formyl, carboxyl, cyano, thiocyanato, $(C_1-C_4)$alkyl, cyano-$(C_1-C_4)$alkyl, $(C_1-C_4)$alkoxy, $(C_1-C_4)$alkylamino, di-[$(C_1-C_4)$alkyl]-amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-[$(C_1-C_4)$alkyl]-amino-$(C_1-C_4)$alkyl, $(C_3-C_9)$-cycloalkylamino-$(C_1-C_4)$alkyl, $(C_3-C_9)$-cycloalkyl, heterocyclyl-$(C_1-C_4)$alkyl having 3 to 9 ring members, the cyclic groups in 3 latter radicals being unsubstituted or substituted by one or more radicals selected from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxy-carbonyl-$(C_1-C_4)$alkyl, $(C_1-C_4)$alkylamino-carbonyl-$(C_1-C_4)$alkyl, $(C_1-C_4)$alkyl-carbonyl, $(C_1-C_4)$alkoxy-carbonyl, aminocarbonyl, $(C_1-C_4)$alkylamino-carbonyl, phenoxy-$(C_1-C_4)$alkyl, phenyl-$(C_1-C_4)$alkyl, heterocyclyl, heterocyclyl-amino, heterocyclyloxy, heterocyclylthio, or one of the 16 latter radicals which is substituted in the acyclic moiety or in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkyl-carbonyl, $(C_1-C_4)$alkoxy-carbonyl and $(C_1-C_4)$alkoxy, and wherein heterocyclyl is a radical containing in each case 3 to 9 ring atoms and 1 hetero-ring atom selected from the group consisting of N, O and S, or is a radical selected from the group consisting of pyrimidinyl, pyridazinyl, pyrazinyl, thiazolyl, oxazolyl, imidazolyl, piperidyl, piperazinyl, dioxolanyl and morpholinyl, or $R^7$ and $R^8$ together are an alkylene chain having 2 to 4 carbon atoms, which is substituted by one or more radicals selected from the group consisting of halogen, $(C_1-C_4)$alkyl and oxo, $R^9$, if n is 1, and the radicals $R^9$, independently at each occurrence, if n is greater than 1, is or are hydrogen, halogen, hydroxyl, amino, nitro, formyl, carboxyl, cyano, thiocyanato, $(C_1-C_4)$alkyl, cyano-$(C_1-C_4)$alkyl, $(C_1-C_4)$alkoxy, $(C_1-C_4)$alkylamino, di-[$(C_1-C_4)$alkyl]-amino, halo-$(C_1-C_4)$alkyl, hydroxy-$(C_1-_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-[$(C_1-C_4)$alkyl]-amino-$(C_1-C_4)$alkyl, $(C_3-C_9)$-cycloalkylamino-$(C_1-C_4)$alkyl, $(C_3-C_9)$-cycloalkyl, heterocyclyl-$(C_1-C_4)$alkyl having 3 to 9 ring members, the cyclic groups in 3 latter radicals being unsubstituted or substituted by one or more radicals selected from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxy-carbonyl-$(C_1-C_4)$alkyl, $(C_1-C_4)$alkylamino-carbonyl-$(C_1-C_4)$alkyl, $(C_1-C_4)$alkyl-carbonyl, $(C_1-C_4)$alkoxy-carbonyl, aminocarbonyl, $(C_1-C_4)$alkylamino-carbonyl, phenoxy-$(C_1-C_4)$alkyl, phenyl-$(C_1-C_4)$alkyl, heterocyclyl, heterocyclyl-amino, heterocyclyloxy, heterocyclylthio, or one of the 16 latter radicals which is substituted in the acyclic moiety or in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkyl-carbonyl, $(C_1-C_4)$alkoxy-carbonyl and $(C_1-C_4)$alkoxy, and wherein heterocyclyl is a radical containing in each case 3 to 9 ring atoms and 1 hetero-ring atom selected from the group consisting of N, O and S, or is a radical selected from the group consisting of pyrimidinyl, pyridazinyl, pyrazinyl, thiazolyl, oxazolyl, imidazolyl, piperidyl, piperazinyl, dioxolanyl and morpholinyl, or two adjacent radicals $R^9$ are a fused-on ring having 4 to 6 ring atoms which is carbocyclic or optionally one of these ring atoms is a hetero-ring atom selected from the group consisting of O, S and N, or if two of these ring atoms are replaced by a hetero-ring atom form a piperidyl, piperazinyl, dioxolanyl or morpholinyl fused-on ring, and said fused-on rings are unsubstituted or substituted by one or more radicals selected from the group consisting of halogen, $(C_1-C_4)$alkyl and oxo, X is a group of the formula —O—, $S(O)_q$—, —NR*— or —N(O)—, in which q is 0, 1 or 2 and R* is hydrogen or alkyl having 1 to 4 carbon atoms, or a group of the formula $CR^{13}R^{14}$ in which the definitions of $R^{13}$ and $R^{14}$ are selected from the radicals recited for $R^2$ and $R^3$, Y is a direct bond or a group of the formula —O—, $S(O)_r$—, —NR— or —N(O)—, in which r is 0, 1 or 2 and R is hydrogen or alkyl having 1 to 4 carbon atoms, or a group of the formula —$CH_2$—, —$C(CH_3)$H— or —$C(CH_3)_2$—, m is 1, 2, 3 or 4, and n is 0, 1, 2, 3, 4 or 5.

2. A compound of the formula (I) or salt thereof as claimed in claim 1, wherein $R^1$ is hydrogen, halogen, hydroxyl, amino, $(C_1-C_4)$alkyl, $(C_1-C_4)$alkoxy, $(C_1-C_4)$alkylamino, di-[$(C_1-C_4)$alkyl]-amino, halo-$(C_1-C_4)$alkyl, $(C_1-C_4)$alkoxy-$C_1-C_4$) alkyl, $(C_2-C_6)$alkenyl, $(C_2-C_6)$alkynyl, phenyl, phenoxy or a phenyl or phenoxy radical which is substituted in the phenyl moiety by one or more radicals from the group consisting of halogen, $(C_1-C_4)$alkyl, $(C_1-C_4)$alkoxy and $(C_1-C_4)$alkoxy-carbonyl, $R^2$ and $R^3$ independently of one another are hydrogen, halogen, hydroxyl, amino, $(C_1-C_4)$alkyl, $(C_1-C_4)$alkoxy, $(C_1-C_4)$alkylamino, di-[$(C_1-C_4)$alkyl]-amino, halo-$(C_1-C_4)$alkyl, $(C_1-C_4)$alkoxy-$(C_1-C_4)$alkyl, $(C_2-C_6)$alkenyl, $(C_2-C_6)$alkynyl, phenyl or phenoxy or a phenyl or phenoxy radical which is substituted in the phenyl moiety by one or more radicals from the group consisting of halogen, $(C_1-C_4)$alkyl, $(C_1-C_4)$alkoxy and $(C_1-C_4)$alkoxy-carbonyl, or $R^2$ and $R^3$, together with the carbon atom of the group $CR^2R^3$, are a saturated carbocyclic radical having 3 to 6 ring members which is unsubstituted or substituted by one or more radicals from the group consisting of $(C_1-C_4)$alkyl, halogen and oxo, $R^4$ and $R^5$ independently of one another are hydrogen, amino, formyl, $(C_1-C_4)$alkyl, $(C_1-C_4)$alkoxy-$(C_1-C_4)$ alkyl, $(C_2-C_6)$alkenyl, $(C_2-C_6)$alkynyl, $(C_1-C_4)$ alkylamino-$(C_1-C_4)$alkyl, di-$[(C_1-C_4)$alkyl]-amino-$(C_1-C_4)$alkyl or phenyl, phenyl-$(C_1-C_4)$alkyl or phenoxy-carbonyl or one of the three latter radicals which is substituted in the phenyl moiety up to three times by radicals from the group consisting of halogen, $(C_1-C_4)$alkyl, $(C_1-C_4)$alkoxy and $(C_1-C_4)$alkoxy-carbonyl, or $R^4$ and $R^5$, together with the nitrogen atom of the group $NR^4R^5$, form a heterocyclic radical having 3 to 6 ring atoms and, in addition to the N atom, optionally one of these ring atoms is a hetero-ring atom, selected from the group consisting of N and O, and said radicals are unsubstituted or substituted by one or more radicals from the group consisting of halogen, $(C_1-C_4)$alkyl and oxo, $R^6$ is hydrogen, amino, formyl, $(C_1-C_4)$, alkyl, di-$[(C_1-C_4)$alkyl]-amino, $(C_1-C_4)$alkoxy-$(C_1-C_4)$alkyl, $(C_2-C_6)$alkenyl, $(C_2-C_6)$alkynyl, $(C_1-C_4)$ dialkylamino-$(C_1-C_4)$alkyl, phenyl, phenoxy-$(C_1-C_4)$ alkyl, phenyl-$(C_1-C_4)$alkyl, phenoxy-carbonyl, phenylamino-carbonyl or one of the five latter radicals which is substituted in the phenyl moiety from one to three times by radicals from the group consisting of halogen, $(C_1-C_4)$alkyl, $(C_1-C_4)$alkoxy and $(C_1-C_4)$ alkoxy-carbonyl, $R^7$ and $R^8$ independently of one another are hydrogen, $(C_1-C_4)$alkyl, $(C_1-C_4)$alkoxy-$(C_1-C_4)$alkyl, $(C_2-C_6)$ alkenyl, $(C_2-C_6)$alkynyl, di-$[(C_1-C_4)$alkyl]-amino-$(C_1-C_4)$alkyl, phenyl, phenoxy-$(C_1-C_4)$alkyl, phenyl-$(C_1-C_4)$alkyl or one of the three latter radicals, which is substituted in the phenyl moiety from one to three times by radicals from the group consisting of halogen, $(C_1-C_4)$alkyl, $(C_1-C_4)$alkoxy and $(C_1-C_4)$alkoxy-carbonyl, or $R^7$ and $R^8$ together are an alkylene chain having 2 to 4 carbon atoms, which is unsubstituted or substituted by one or more radicals from the group consisting of halogen, $(C_1-C_4)$alkyl and oxo, $R^9$ independently at each occurrence is hydrogen, halogen, hydroxyl, amino, nitro, cyano, $(C_1-C_4)$alkyl, $(C_1-C_4)$alkoxy, $(C_1-C_4)$alkylamino, di-$[(C_1-C_4)$alkyl]-amino, perhalo-$(C_1-C_4)$alkyl, hydroxy-$(C_1-C_4)$alkyl, $(C_1-C_4)$alkoxy-$(C_1-C_4)$alkyl, $(C_1-C_4)$alkylthio, $(C_2-C_6)$alkenyl, $(C_2-C_6)$alkynyl, di-$[(C_1-C_4)$alkyl]-amino-$(C_1-C_4)$alkyl, phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$ alkylcarbonyl, $(C_1-C_4)$alkyloxycarbonyl, phenoxy-$(C_1-C_4)$alkyl, phenyl-$(C_1-C_4)$alkyl, heterocyclyl, heterocyclylamino, heterocyclyloxy, heterocyclylthio or one of the 13 latter radicals which is substituted in the acyclic moiety or, preferably, in the cyclic moiety by one or more radicals from the group consisting of halogen, $(C_1-C_4)$alkyl, $(C_1-C_4)$alkoxy, $(C_1-C_4)$ alkylthio, $(C_1-C_4)$haloalkyl, $(C_1-C_4)$haloalkoxy and $(C_1-C_4)$alkoxy-carbonyl, wherein heterocyclyl is a radical having 3 to 6 ring atoms and 1 hetero-ring atom from the group consisting of N and O, or is a radical selected from the group consisting of pyrimidinyl, pyridazinyl, pyrazinyl, thiazolyl, oxazolyl, imidazolyl, piperidyl, piperazinyl, dioxolanyl and morpholinyl, or two adjacent radicals $R^9$ together are a fused-on ring having 4 to 6 ring atoms which is carbocyclic or optionally one of these ring atoms is a hetero-ring atom from the group consisting of O and N, or if two of these ring atoms are replaced by a hetero-ring atom form a piperidyl, piperazinyl, dioxolanyl, or morpholinyl fused-on ring, said fused-on rings are unsubstituted or substituted by one or more $(C_1-C_4)$alkyl radicals, X is a group of the formula —O— or —NR*—, in which R* is hydrogen or methyl, or a group of the formula $CR^{13}R^{14}$, in which the definitions of $R^{13}$ and $R^{14}$ are selected from the radicals possible for $R^2$ and $R^3$, Y is a direct bond or a group of the formula —O— or —NR—, in which R is hydrogen or methyl.

3. A compound of the formula (I) or salt thereof as claimed in claim 1, wherein $R^1$ is hydrogen, halogen or $(C_1-C_4)$alkyl, $R^2$ and $R^3$ independently of one another are hydrogen, halogen, $(C_1-C_4)$alkyl or phenyl or $R^2$ and $R^3$ together with the carbon atom of the group $CR^2R^3$, are saturated $(C_4-C_6)$cycloalkyl, $R^4$ and $R^5$ independently of one another are hydrogen, amino, formyl or $(C_1-C_4)$alkyl, or $R^4$ and $R^5$ together with the nitrogen atom of the group $NR^4R^5$, form heterocyclic radical having 4 to 6 ring atoms and, in addition to the N atom, optionally one of these ring atoms is a hetero-ring atom, selected from the group consisting of N and O, $R^6$ is hydrogen or $(C_1-C_4)$alkyl, $R^7$ and $R^8$ independently of one another are hydrogen, $(C_1-C_4)$alkyl or $(C_1-C_4)$alkoxy-$(C_1-C_4)$alkyl or $R^7$ and $R^8$ together are an alkylene chain having 2 to 4 carbon atoms, $R^9$ independently at each occurrence is hydrogen, halogen, hydroxyl, $(C_1-C_4)$alkyl or $(C_1-C_4)$alkoxy, m is 1 or 2, n is 2 or 3, X is a group of the formula —O— or —NH—, or a group of the formula $CR^{13}R^{14}$, in which the definitions of $R^{13}$ and $R^{14}$ are selected from the radicals possible for $R^2$ and $R^3$, Y is a direct bond or a group of the formula —O— or —NH—.

4. A compound of the formula I or a salt thereof as claimed in claim 1, wherein

X is a group of the formula —O—, —S—, or —NR*—, in which R* is hydrogen or allyl having 1 to 4 carbon atoms, or a group of the formula $CR^{13}R^{14}$, in which the definition of $R^{13}$ and $R^{14}$ are selected from the radical recited for $R^2$ and $R^3$, Y is a direct bond or a group of the formula —O—, —S—, or —NR—, in which R is hydrogen or allyl having 1 to 4 carbon atoms, or a group of the formula —$CH_2$—, —$C(CH_3)H$— or —$C(CH_3)_2$—.

5. A compound of the formula (I) or salt thereof as claimed in claim 1, wherein $R^1$ is hydrogen, halogen or $(C_1-C_4)$alkyl, $R^2$ and $R^3$ independently of one another are hydrogen, halogen, $(C_1-C_4)$alkyl or phenyl or $R^2$ and $R^3$ together with the carbon atom of the group $CR^2R^3$, are saturated $(C_4-C_6)$cycloalkyl, $R^4$ and $R^5$ are hydrogen atoms, or NR$^4$R$^5$ is piperidinyl, pyrrolidinyl or morpholinyl, R$^6$ is hydrogen or (C$_1$–C$_4$)alkyl, R$^7$ is hydrogen or (C$_1$–C$_4$)alkyl, R$^8$ is hydrogen, R$^7$ and R$^8$ together are an alkylene chain having 2 to 4 carbon atoms, R$^9$ independently at each occurrence is hydrogen, halogen, hydroxyl, (C$_1$–C$_4$)alkyl or (C$_1$–C$_4$)alkoxy, m is 1 or 2, n is 2 or 3, X is a group of the formula —O— or —NH—, or a group of the formula CR$^{13}$R$^{14}$, in which R$^{13}$ is hydrogen, halogen, (C$_1$–C$_4$)alkyl or phenyl and R$^{14}$ is hydrogen, halogen, (C$_1$–C$_4$)alkyl or phenyl or CR$^{13}$R$^{14}$ is saturated (C$_4$–C$_6$)cycloalkyl, Y is a direct bond or a group of the formula —O— or —NH—.

6. A compound of the formula (I) or salt thereof as claimed in claim 1, wherein

R$^1$ is hydrogen, halogen or (C$_1$–C$_4$)alkyl,

R$^2$ and R$^3$ independently of one another are hydrogen, halogen or (C$_1$–C$_4$)alkyl or R$^4$ and R$^5$ are hydrogen atoms, R$^6$ is hydrogen, R$^7$ is hydrogen, methyl or ethyl, R$^8$ is hydrogen, R$^9$ independently at each occurrence is hydrogen, halogen, hydroxyl, (C$_1$–C$_4$)alkyl or (C$_1$–C$_4$)alkoxy, m is 1 or 2, n is 2 or 3, X is a group of the formula —O— or a group of the formula CR$^{13}$R$^{14}$, in which R$^{13}$ is hydrogen, halogen, methyl, and R$^{14}$ is hydrogen, halogen, or methyl CR$^{13}$R$^{14}$ is saturated (C$_4$–C$_6$)cycloalkyl, Y is a direct bond or a group of the formula —O—.

7. A herbicidal or plant growth-regulating composition, which comprises one or more compound of the formula (I) or salt thereof as defined in claim 1 and formulation auxiliaries which are customary in plant protection.

8. A method of combating weeds or of regulating the growth of plants, which comprises applying an effective quantity of one or more compound of the formula (I) or a salt thereof as defined in claim 1 to the weeds or plants, their seeds or the area on which they grow.

* * * * *